(12) United States Patent
Spiro

(10) Patent No.: US 11,172,625 B2
(45) Date of Patent: Nov. 16, 2021

(54) INTEGRATED CEILING DEVICE WITH MECHANICAL ARRANGEMENT FOR A LIGHT SOURCE

(71) Applicant: Daniel S. Spiro, Scottsdale, AZ (US)

(72) Inventor: Daniel S. Spiro, Scottsdale, AZ (US)

(73) Assignee: LIGHTING DEFENSE GROUP, LLC, Scottsdale, AZ (US)

( * ) Notice: Subject to any disclaimer, the term of this patent is extended or adjusted under 35 U.S.C. 154(b) by 0 days.

(21) Appl. No.: 17/032,650

(22) Filed: Sep. 25, 2020

(65) Prior Publication Data

US 2021/0018002 A1 Jan. 21, 2021

Related U.S. Application Data

(63) Continuation of application No. 16/883,028, filed on May 26, 2020, which is a continuation of application
(Continued)

(51) Int. Cl.
*A01H 5/10* (2018.01)
*F21V 33/00* (2006.01)
(Continued)

(52) U.S. Cl.
CPC ............. *A01H 5/10* (2013.01); *F04D 19/002* (2013.01); *F04D 29/582* (2013.01); *F21K 9/232* (2016.08);
(Continued)

(58) Field of Classification Search
CPC ...... F21V 7/0016; F21V 29/777; F21V 29/77; F21V 29/70; F21V 29/83; F21V 15/01;
(Continued)

(56) References Cited

U.S. PATENT DOCUMENTS 5,580,158 A 12/1996 Aubrey et al.
6,029,092 A 2/2000 Stein
(Continued)

FOREIGN PATENT DOCUMENTS

WO WO 2008/146232 12/2008

OTHER PUBLICATIONS

Holophanse Lighting, Phuzion, http://www.holophane.com/products/Family.asp?Brand=HLP&Family=Phuzion&ProductType=Indoor&Category=Performance%20HID&SubCategory=High%20Bays, downloaded Dec. 26, 2013.

*Primary Examiner* — Erin Kryukova
(74) *Attorney, Agent, or Firm* — Barnes & Thornburg LLP; Irina N. Sullivan; Michael A. Carrillo

(57) ABSTRACT

An integrated ceiling device (80, 120) includes an electronics assembly (56) and a mechanical arrangement (20). The mechanical arrangement includes a housing (22), a heat dissipating structure (24), and support arms (26). The housing is configured to retain the electronics assembly. The heat dissipating structure includes a lamp seat (50) for receiving a light source (54), and a central opening (34) surrounded by fins (36). The support arms extend between and interconnect the housing with the heat dissipating structure. The housing is positioned within the central opening and is spaced apart from the fins of the heat dissipating structure to enable a free flow of air in an air gap (42) between the housing (22) and the structure (24). The electronics assembly may include a plurality of elements (160, 162, 164, 166) retained in the housing which are spaced apart from the heat dissipating structure.

24 Claims, 24 Drawing Sheets

Related U.S. Application Data

No. 15/089,146, filed on Apr. 1, 2016, now Pat. No. 10,677,446, which is a continuation of application No. 14/151,245, filed on Jan. 9, 2014, now Pat. No. 9,441,634.

(60) Provisional application No. 61/751,660, filed on Jan. 11, 2013.

(51) Int. Cl.

| | |
|---|---|
| *F04D 19/00* | (2006.01) |
| *F21V 29/74* | (2015.01) |
| *F04D 29/58* | (2006.01) |
| *H05B 47/16* | (2020.01) |
| *H05B 47/105* | (2020.01) |
| *F21V 7/24* | (2018.01) |
| *F21V 21/03* | (2006.01) |
| *F21V 7/22* | (2018.01) |
| *H05B 45/12* | (2020.01) |
| *H05B 45/10* | (2020.01) |
| *F21V 29/77* | (2015.01) |
| *F21S 8/02* | (2006.01) |
| *F21V 21/04* | (2006.01) |
| *F21V 29/70* | (2015.01) |
| *H04N 7/18* | (2006.01) |
| *F21K 9/232* | (2016.01) |
| *F21V 29/508* | (2015.01) |
| *F21S 8/06* | (2006.01) |
| *F21V 13/04* | (2006.01) |
| *F21V 15/01* | (2006.01) |
| *F21V 21/08* | (2006.01) |
| *F21V 23/00* | (2015.01) |
| *F21V 23/02* | (2006.01) |
| *F21V 29/83* | (2015.01) |
| *F21V 7/00* | (2006.01) |
| *F21Y 115/10* | (2016.01) |
| *H05B 47/19* | (2020.01) |
| *H05B 47/115* | (2020.01) |

(52) U.S. Cl.
CPC ........... *F21S 8/026* (2013.01); *F21S 8/06* (2013.01); *F21V 7/00* (2013.01); *F21V 7/22* (2013.01); *F21V 7/24* (2018.02); *F21V 13/04* (2013.01); *F21V 15/01* (2013.01); *F21V 21/03* (2013.01); *F21V 21/047* (2013.01); *F21V 21/0832* (2013.01); *F21V 23/002* (2013.01); *F21V 23/02* (2013.01); *F21V 29/508* (2015.01); *F21V 29/70* (2015.01); *F21V 29/74* (2015.01); *F21V 29/77* (2015.01); *F21V 29/777* (2015.01); *F21V 29/83* (2015.01); *F21V 33/0056* (2013.01); *F21V 33/0076* (2013.01); *F21V 33/0096* (2013.01); *H04N 7/188* (2013.01); *H05B 45/10* (2020.01); *H05B 45/12* (2020.01); *H05B 47/105* (2020.01); *H05B 47/16* (2020.01); *F21V 33/00* (2013.01); *F21Y 2115/10* (2016.08); *H05B 47/115* (2020.01); *H05B 47/19* (2020.01)

(58) Field of Classification Search
CPC ...... F21V 23/002; F21V 23/02; F21V 23/023; F21V 21/047; F21Y 2105/18; F21Y 2107/90; F21S 8/06; F21S 8/026; F21S 8/04

See application file for complete search history.

(56) References Cited

U.S. PATENT DOCUMENTS

| | | | |
|---|---|---|---|
| 6,132,066 A | 10/2000 | Freedman et al. | |
| 7,619,538 B1 | 11/2009 | Zarian et al. | |
| 7,726,846 B2 | 6/2010 | Yang et al. | |
| 7,753,556 B1 | 7/2010 | Zhang | |
| 7,871,184 B2 | 1/2011 | Peng | |
| 8,087,804 B2* | 1/2012 | Sun | F21V 29/763 362/294 |
| 8,172,435 B2 | 5/2012 | Spiro et al. | |
| 8,246,213 B2 | 8/2012 | Fu | |
| 8,260,575 B2 | 9/2012 | Walters et al. | |
| 8,272,765 B2 | 9/2012 | Ter-Hovhannisyan | |
| 8,297,798 B1* | 10/2012 | Pittman | F21V 7/28 362/296.05 |
| 8,373,362 B2 | 2/2013 | Chemel et al. | |
| 8,531,134 B2 | 9/2013 | Chemel et al. | |
| 8,552,666 B2 | 10/2013 | Wendt et al. | |
| 9,441,634 B2 | 9/2016 | Spiro | |
| 9,626,847 B2 | 4/2017 | Spiro | |
| 9,885,451 B2 | 2/2018 | Spiro | |
| 9,939,143 B2 | 4/2018 | Spiro | |
| 9,990,817 B2 | 6/2018 | Spiro | |
| 2002/0152298 A1 | 10/2002 | Kikta | |
| 2008/0285271 A1* | 11/2008 | Roberge | F21V 29/677 362/235 |
| 2008/0309486 A1 | 12/2008 | McKenna | |
| 2009/0263232 A1 | 10/2009 | Jarrah | |
| 2010/0002452 A1 | 1/2010 | Gananathan | |
| 2010/0277105 A1* | 11/2010 | Oyama | H05B 47/11 315/312 |
| 2010/0282446 A1* | 11/2010 | Yamamoto | F21S 8/02 165/109.1 |
| 2010/0327766 A1 | 12/2010 | Recker | |
| 2011/0002116 A1 | 1/2011 | Chen | |
| 2011/0037368 A1* | 2/2011 | Huang | F21K 9/232 313/46 |
| 2011/0194282 A1 | 8/2011 | Paik et al. | |
| 2011/0222291 A1* | 9/2011 | Peng | F21V 21/02 362/294 |
| 2011/0242828 A1* | 10/2011 | Blincoe | F21V 23/008 362/373 |
| 2011/0249441 A1* | 10/2011 | Donegan | F21V 29/77 362/253 |
| 2011/0309751 A1 | 12/2011 | Ter-Hovhannisyan | |
| 2012/0033419 A1* | 2/2012 | Kim | F21V 29/02 362/235 |
| 2012/0113642 A1 | 5/2012 | Catalano | |
| 2012/0206050 A1 | 8/2012 | Spero | |
| 2012/0212945 A1* | 8/2012 | Frank | F21V 29/773 362/184 |
| 2012/0250302 A1 | 10/2012 | Edwards et al. | |
| 2012/0275162 A1 | 11/2012 | Spiro | |
| 2012/0293309 A1 | 11/2012 | Spiro et al. | |
| 2013/0039041 A1* | 2/2013 | Yeh | F21S 8/04 362/147 |
| 2013/0044478 A1 | 2/2013 | Steedly | |
| 2013/0107041 A1 | 5/2013 | Norem | |
| 2013/0107517 A1 | 5/2013 | Shih | |
| 2013/0300290 A1 | 11/2013 | Holland et al. | |
| 2014/0021884 A1 | 1/2014 | Fetterly | |
| 2014/0035482 A1 | 2/2014 | Rains, Jr. | |
| 2014/0355302 A1 | 12/2014 | Wilcox | |
| 2014/0375206 A1 | 12/2014 | Holland | |
| 2015/0131287 A1* | 5/2015 | Marsh | F21V 15/01 362/260 |

\* cited by examiner

INTEGRATED CEILING DEVICE WITH MECHANICAL ARRANGEMENT FOR A LIGHT SOURCE

CROSS REFERENCE TO RELATED APPLICATION(S)

This application is a continuation of the earlier U.S. Utility patent application entitled "INTEGRATED CEILING DEVICE WITH MECHANICAL ARRANGEMENT FOR A LIGHT SOURCE," Ser. No. 16/883,028, filed May 26, 2020, which is a continuation of the earlier U.S. Utility patent application entitled "INTEGRATED CEILING DEVICE WITH MECHANICAL ARRANGEMENT FOR A LIGHT SOURCE," Ser. No. 15/089,146, filed Apr. 1, 2016, which is a continuation of the earlier U.S. Utility patent application entitled "INTEGRATED CEILING DEVICE WITH MECHANICAL ARRANGEMENT FOR A LIGHT SOURCE," Ser. No. 14/151,245, filed Jan. 9, 2014, which claims priority to U.S. Provisional Patent Application entitled "DEVICE INTEGRATED AUTOMATED LUMINAIRE AND METHOD OF OPERATION," Ser. No. 61/751,660, filed Jan. 11, 2013, the disclosures of which are hereby incorporated entirely herein by reference.

TECHNICAL FIELD OF THE INVENTION

The present invention relates generally to integrated ceiling device technology including lighting. More specifically, the present invention relates to an integrated ceiling device including a mechanical arrangement for a light emitting diode (LED) light source having effective heat dissipation capability and efficient optics.

BACKGROUND OF THE INVENTION

Historically, the building industry has employed a large number of professions to design, manufacture, and maintain building systems that perform a variety of functions. These various functions include, for example, lighting control, smoke detection, air quality monitoring, occupancy awareness, and so forth. Each individual system carries with it costs associated with upfront equipment purchase, installation, operation, and maintenance. While cost control is important, additional factors such as aesthetic appeal, ease of use and maintenance, expandability, and so forth can be equivalently critical in the design, manufacture, operation, and maintenance of a variety building systems.

Increasingly, industry is focusing on intelligent systems or smart systems to provide a variety of building system functions. Unfortunately, these intelligent systems can be costly, complex, and difficult to maintain. Moreover, due at least in part to historical legacy, few advances have been made in offering building owners efficient, economical, and aesthetically pleasing smart building solutions.

According to an aspect of this disclosure, an integrated ceiling device includes a mechanical arrangement having a housing retaining an electrical assembly and a heat sink having a plurality of monolithically formed heat dissipating fins, such that the housing extends partially above the heat sink and is positioned about a vertical axis of the heat sink, and the housing is coupled to the heat sink to form a through air gap extending between the housing and the heat sink. Also, according to this aspect, at least one light source is thermally coupled to and disposed on the heat sink.

According to another aspect of this disclosure, an integrated ceiling device includes a mechanical arrangement having a housing retaining an electrical assembly and a heat sink having monolithically formed heat dissipating fins, such that the housing is positioned partially above the heat sink and is configured about an interior vertical axis of the heat sink, and the housing is coupled to the heat sink to form an air pass through extending between the housing and the heat sink. This aspect further includes a plurality of light sources thermally coupled to the heat sink such that warmed air generated by the heatsink dissipating heat from the plurality of light sources is directed around the housing by the mechanical arrangement.

According to yet another aspect of this disclosure, an integrated ceiling device includes an electronics assembly and a mechanical arrangement having a housing retaining the electronics assembly, a heat sink having a central through opening wherein the housing is coupled to the heat sink to form a through air gap extending between the housing and the heat sink, and a light source coupled to the heat sink. Further, in accordance with this aspect, the light source is separated from the housing by the through air gap, the integrated ceiling device operates in response to supplying power to the integrated ceiling device, and cooling the electronics assembly is in response to free flow of air flowing through the integrated ceiling device.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, the Figures are not necessarily drawn to scale, and:

DETAILED DESCRIPTION

Figure 1:
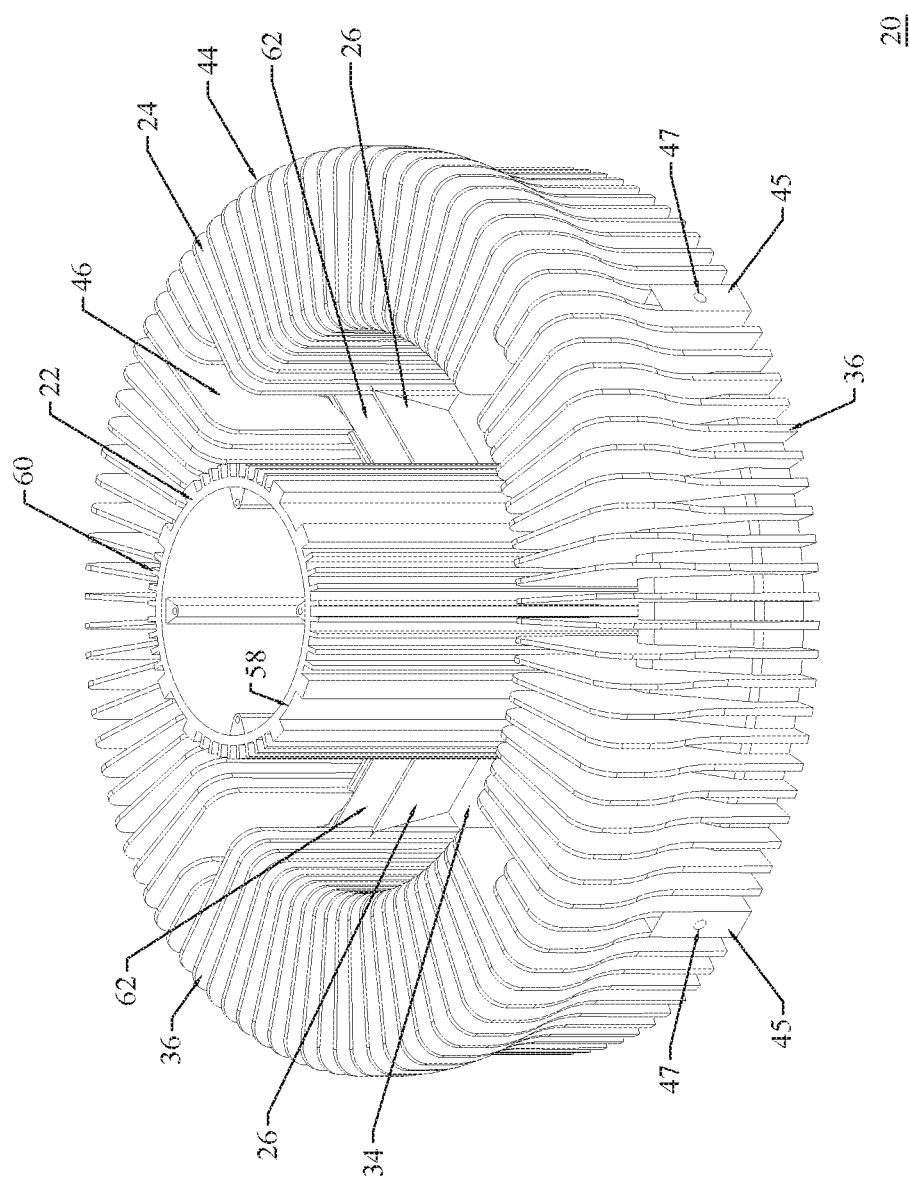
FIG. 1 shows a top perspective view of a mechanical arrangement for an integrated ceiling device, i.e., a LEAM, in accordance with an embodiment.

Suitable ambient lighting is a quintessential need in virtually every building system application, and the lighting industry is rapidly migrating from traditional light sources such as fluorescent, high intensity discharge (HID), and incandescent lamps to solid state lighting, such as light-emitting diodes (LEDs). Light fixtures (technically referred to as luminaires in accordance with International Electrotechnical Commission terminology) employing LEDs initially appeared in small devices utilized in low light output applications. Increasingly, light fixtures employing LEDs can be found in indoor commercial applications, such as predominantly high-end offices, institutional spaces, and supermarkets' refrigerated spaces. In exterior applications, municipalities and some large box retailers have begun replacing their traditional street and pole mounted light fixtures with fixtures employing LEDs. LED technology is also being embraced by the automotive and aircraft industries.

An LED lamp is a solid state device. The solid state technology can enable device integration in an un-paralleled manner thus leading to opportunities in the areas of efficient energy usage, efficient use of human resources, safer and more pleasant illumination, and better use of material resources. Indeed, light fixtures employing LEDs are fast emerging as a superior alternative to conventional light fixtures because of their low energy consumption, long operating life, optical efficiency, durability, lower operating costs, and so forth.

There are presently a number of technical and economic problems associated with the implementation of high-output LED light fixtures in the market. The LED lamp cost is high when compared with traditional light sources. Smaller LED lamps yield higher efficiency. However, to generate high light output with LED lamps, clusters of LED lamps need to be formed. The more LED lamps used, the higher the cost. Additionally, cool operation is essential to the electronics devices and particularly to the LED lamp.

A cluster of high output LED lamps in close proximity to one another generates a significant amount of heat. Thus, implementation of LEDs for many light fixture applications has been hindered by the amount of heat build-up. High temperature reduces the lamp efficiency and may shorten the life of the lamp and other electronic components, eventually causing device failure. Additionally, the life of the LED lamp and its output depends on the surrounding ambient temperature, and most critically, its impact on the lamps' junction temperature. The junction temperature is the temperature where the lamp die is secured to the factures' heat sink. As the heat generated with high output LED lamps increases, so does the difficulty of designing large passive heat sinks that are architecturally attractive, lightweight, and economically feasible. Consequently, effective heat dissipation is an important design consideration for maintaining light output and/or increasing lifespan of the LED light source.

Embodiments of the invention entail an integrated ceiling device and a mechanical arrangement for that provides effective heat dissipation for a number of light sources installed in the integrated ceiling device. For brevity, the integrated ceiling device will be referred to herein as a Local Environmental Area Manager (LEAM). The LEAM, with the mechanical arrangement, is configured to accommodate multiple LED light sources. The mechanical arrangement maintains low junction temperature by effectively conducting heat generated by the LED light sources, also referred to herein as LED lamps, away from other LED lamps and other electronic components. Maintaining a low temperature at this junction yields improvements in lamp energy efficiency and enhanced lifespan for the LED light sources.

Additionally, the configuration of the mechanical arrangement physically isolates the heat dissipating structure of the mechanical arrangement from a housing in which an electronics assembly for the LEAM is housed. As such, the housing may be sized to accommodate a plurality of onboard electronic devices (e.g., camera, occupancy sensor, air quality sensor, smoke detector, and so forth) that are not unduly taxed by the heat produced by the LED light sources. These onboard electronic devices may be configured to emulate human sensory capability and to make actionable decisions based on changing environmental conditions in which the LEAM is located. As such, the LEAM can be a configured as a smart system to provide a variety of building system functions. Accordingly, the LEAM includes key elements that are organized in a manner that resolves the mechanical, thermal, electrical, and architectural challenges that are commonly associated with the design of high-output LED light fixtures and other ceiling mounted devices. Further the structural configuration of the LEAM makes the LEAM suitable for use in a wide variety of environments, such as, commercial, institutional, and industrial applications.

Figure 2:
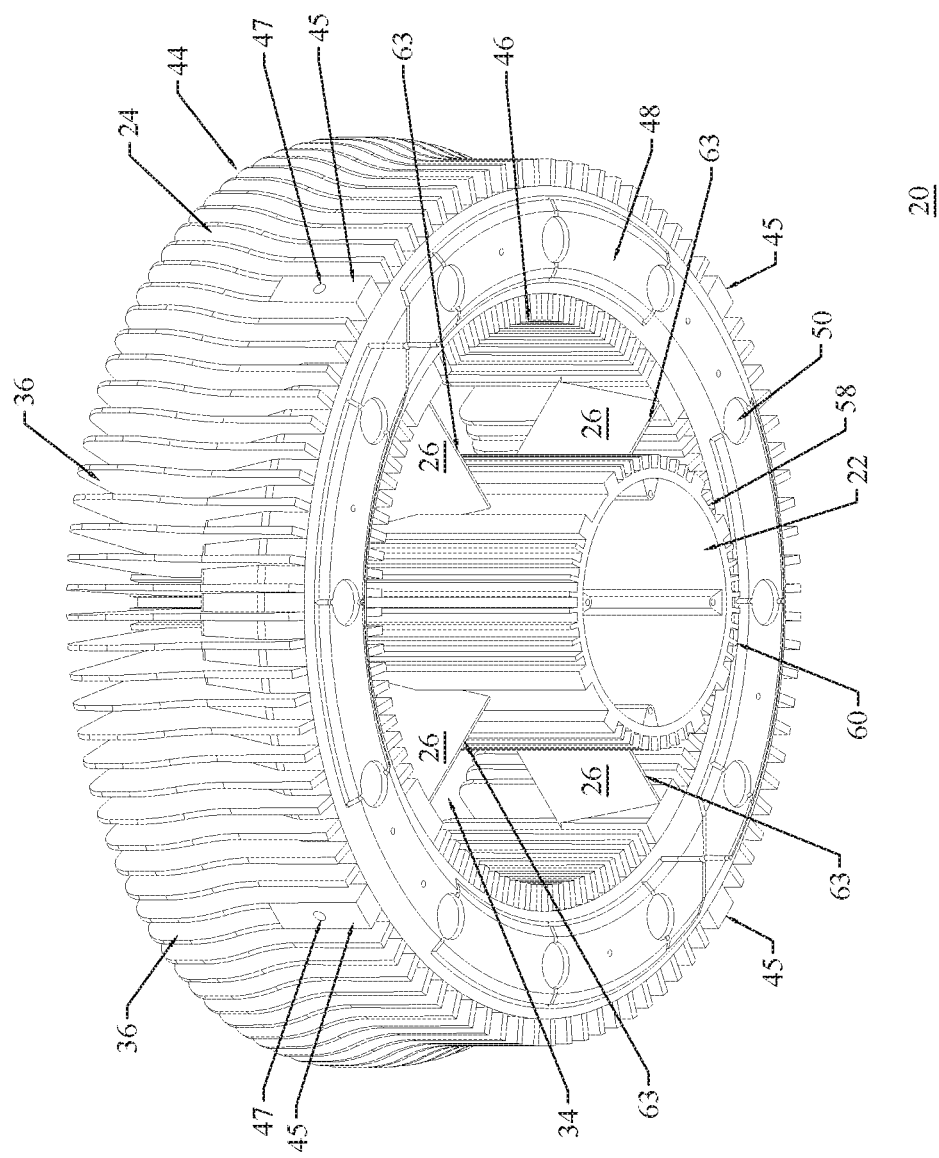
FIG. 2 shows a bottom perspective view of the mechanical arrangement of FIG. 1.
Figure 3:
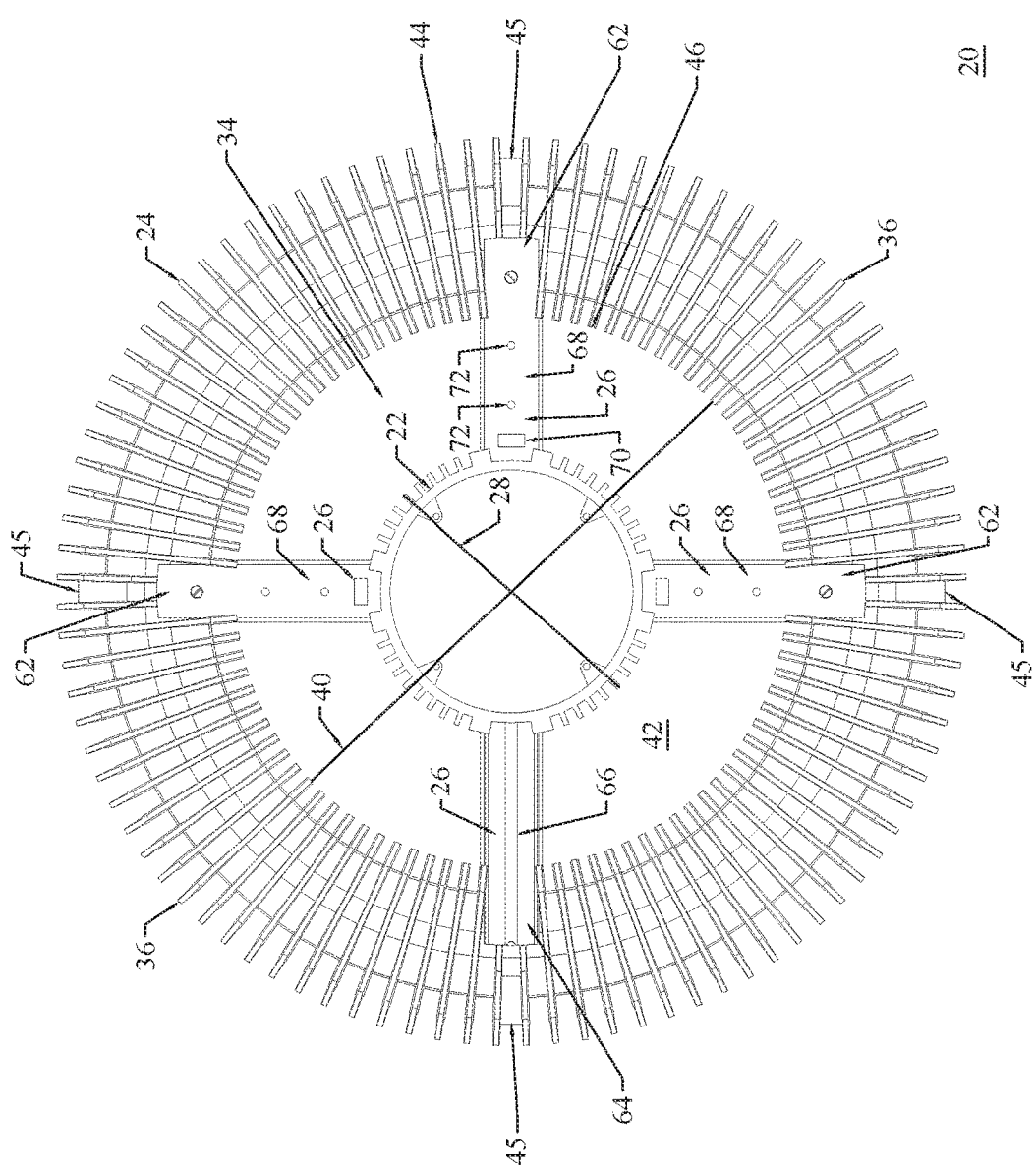
FIG. 3 shows a top view of the mechanical arrangement.
Figure 4:
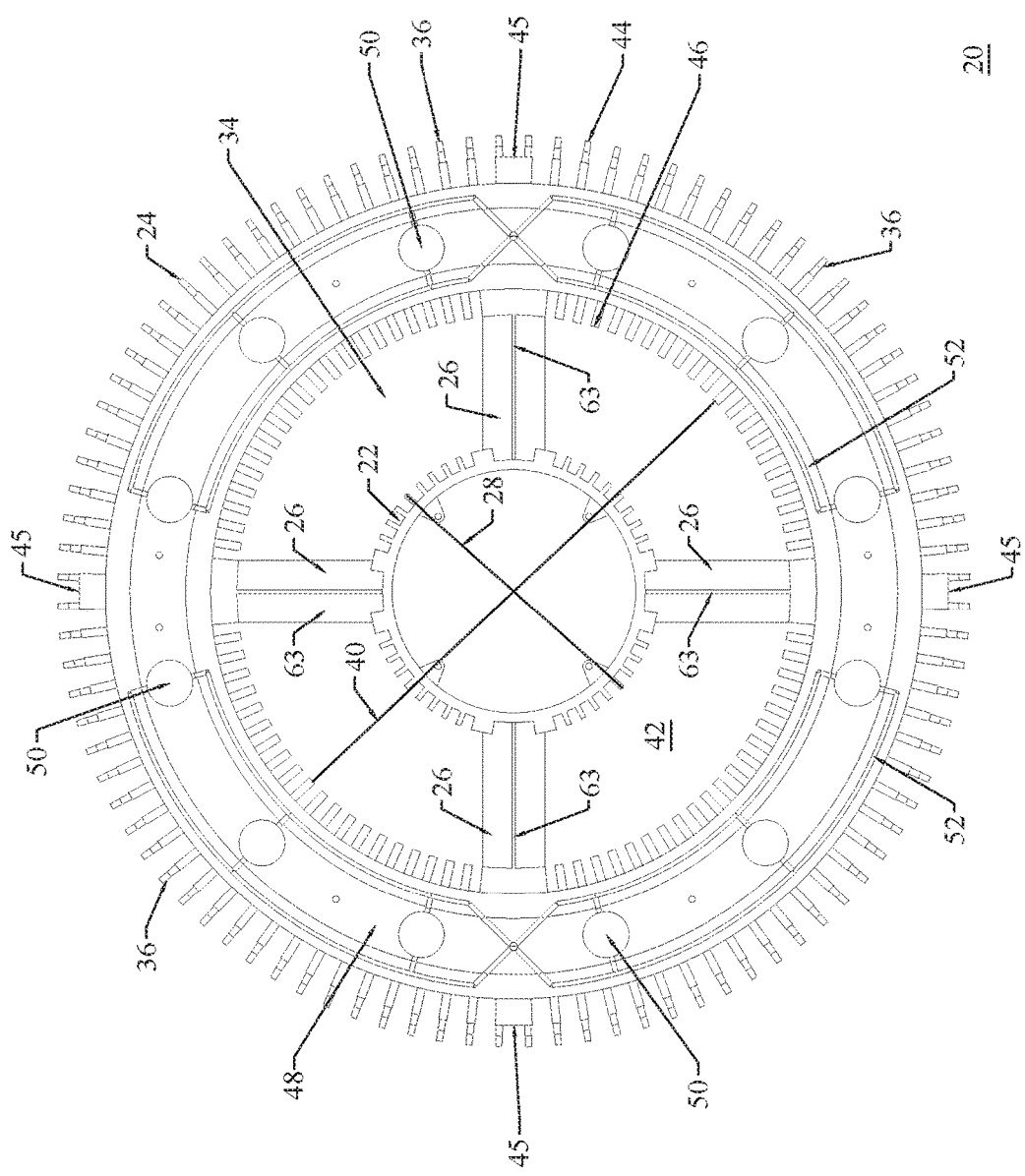
FIG. 4 shows a bottom view of the mechanical arrangement.
Figure 5:
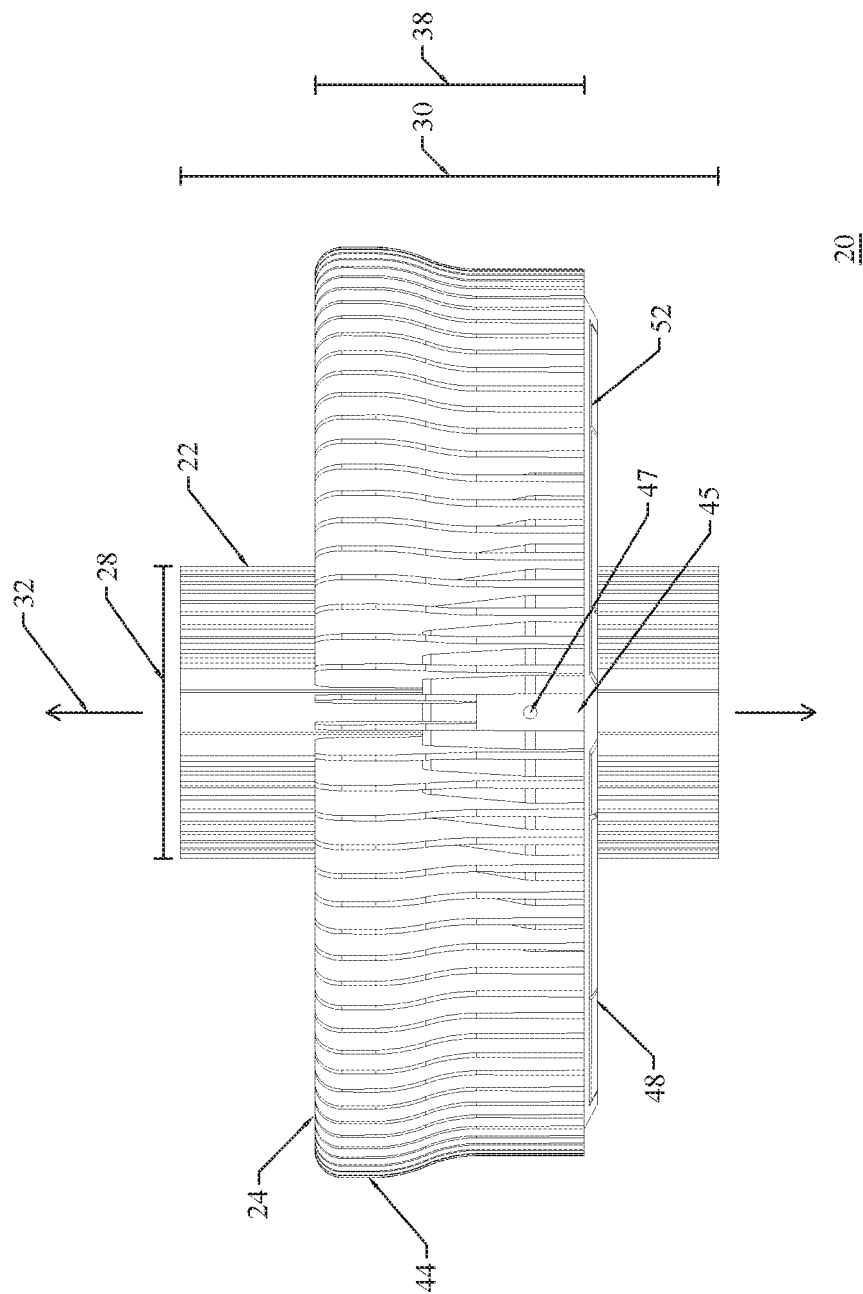
FIG. 5 shows a side view of the mechanical arrangement.
Figure 6:
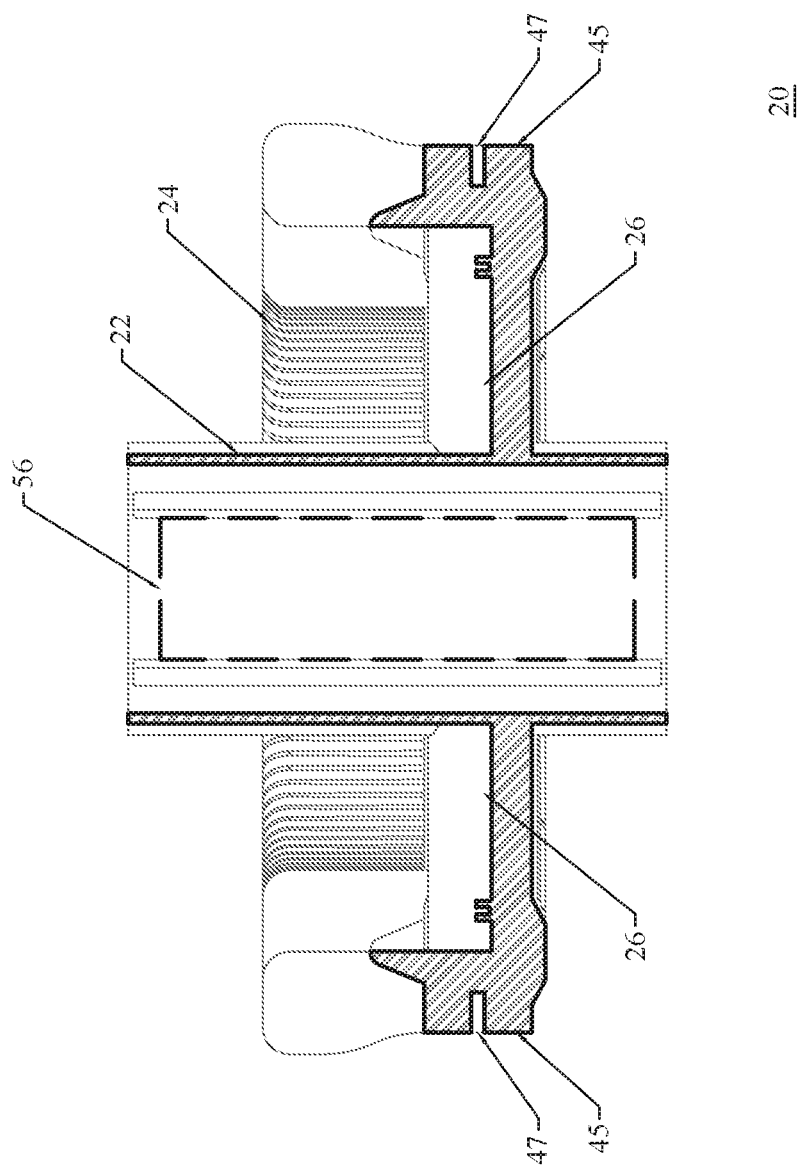
FIG. 6 shows a side sectional view of the mechanical arrangement.

Referring now to FIGS. 1-6, FIG. 1 shows a top perspective view of a mechanical arrangement 20 for an integrated ceiling device, i.e., a LEAM, in accordance with an embodiment. FIG. 2 shows a bottom perspective view of mechanical arrangement 20. FIG. 3 shows a top view of mechanical arrangement, FIG. 4 shows a bottom view of mechanical arrangement 20, FIG. 5 shows a side view of mechanical arrangement, and FIG. 6 shows a side sectional view of mechanical arrangement 20. The inclusion of mechanical arrangement 20 into various LEAM embodiments will be discussed below in connection with FIGS. 7-18.

Mechanical arrangement 20 generally includes a housing 22, a heat dissipating structure 24, and support arms 26. Housing 22, heat dissipating structure 24, and support arms 26 may be monolithically casted or printed, or can be assembled by joining casted and non-casted elements. Heat dissipating structure 24, as well as housing 22 and support arms 26 may be manufactured from a heat dissipating, non-corrosive material and may be painted or otherwise treated to suit architectural needs. The configuration of mechanical arrangement provides a rigid design suitable in adverse environments, and housing 22, heat dissipating structure 24, and support arms 26 are organized in a manner that maximizes air flow across the elements.

With particular reference to FIGS. 3 and 5, housing 22 exhibits a generally cylindrical shape having an outer diameter 28 and a height 30 along a longitudinal axis 32 of mechanical arrangement 20 (see FIG. 5). In alternative architectural configurations, housing 22 need not be cylindrical in shape, but may instead be any other suitable three-dimensional shape. Additionally, housing 22 may be expanded both vertically and horizontally to accommodate device scalability.

Heat dissipating structure 24 includes a central opening 34 surrounded by a plurality of fins 36 having a height 38 (see FIG. 5). Thus, heat dissipating structure 24 is generally ring-shaped, with central opening 34 exhibiting an inner dimension, and more particularly, an inner diameter 40 (best seen in FIGS. 3-4). In the illustrated embodiment, heat dissipating structure 24 is a circular ring-shaped structure corresponding with the shape of housing 22. However, in alternative architectural configurations, heat dissipating structure 24 may have a different surrounding shape, e.g., rectangular, oblong, triangular, and so forth, while still retaining central opening 34. It should be further understood that in alternative architectural configurations, central opening 34 need not be circular, but could instead have another shape corresponding to, or differing from, the shape of housing 22 and/or heat dissipating structure 24.

Housing 22 is positioned within central opening 34, and support arms 26 extend between and interconnect housing 22 with heat dissipating structure 24. Outer diameter 28 of housing 22 is less than inner diameter 40 of central opening 34. Therefore, housing 22 is physically spaced apart from fins 36 by an air gap 42 extending between housing 22 and heat dissipating structure 24. The configuration of fins 36 permits free air flow of no less than two hundred and seventy degrees across its vertical axis and the configuration of housing 22 permits no less than three hundred and twenty degrees of free air flow across its vertical axis and in between support arms 26. In addition, housing 22 and heat dissipating structure 24 are exposed to air at their tops and bottom faces. Thus, air is free to flow between housing 22 and heat dissipating structure 24 and over housing 22 and heat dissipating structure 24 to provide effective cooling. Furthermore, housing 22 and its contents are protected from moving objects in the surrounding area by fins 36 of heat dissipating structure 24.

Outer vertical walls 45 at each quarter section of heat dissipating structure 24 can include bores 47, i.e., a hole or passageway, which can serve as an attachment point for a decorative cover, protective frame, protective reflector frame, and the like (not shown). Additionally, the plurality of fins 36 are spaced about the circumference of heat dissipating structure 24. In particular, fins 36 are generally uniformly distributed about both an outer perimeter 44 and an inner perimeter 46 of heat dissipating structure 24. Thus, fins 36 extend partially into air gap 42 between housing 22 and heat dissipating structure 24. The multitude of fins 36 maximize airflow about heat dissipating structure 24 and thereby facilitate effective heat dissipation.

Heat dissipating structure 24 further includes a generally ring-shaped bottom face 48 (FIGS. 2, 4, and 5) connected with fins 36 and at least one lamp seat 50 formed in bottom face 48. Heat dissipating structure 24 and bottom face 48 may be formed as two separately manufactured components that are bolted, welded, or otherwise coupled together during manufacturing. In the illustrated an embodiment, a plurality of lamp seats 50 are formed in bottom face 48 of heat dissipating structure 24, and are generally uniformly distributed in bottom face 48.

Bottom face 48 further includes recessed channels 52 (FIGS. 2, 4, 5) formed therein. Recessed channels 52 are suitably formed and routed to provide the locations in bottom face 48 for electrically interconnecting each of lamp seats 50. That is, wiring (not shown) may be directed through recessed channels 52 when mechanical arrangement 20 is assembled with other components (discussed below) to form a particular LEAM with lighting capacity. Recessed channels 52 are illustrated in FIGS. 2, 4, 5 for exemplary purposes. In actual practice, recessed channels 52 would not be visible on an exterior surface of bottom face 48 of heat dissipating structure 24.

Figure 8:
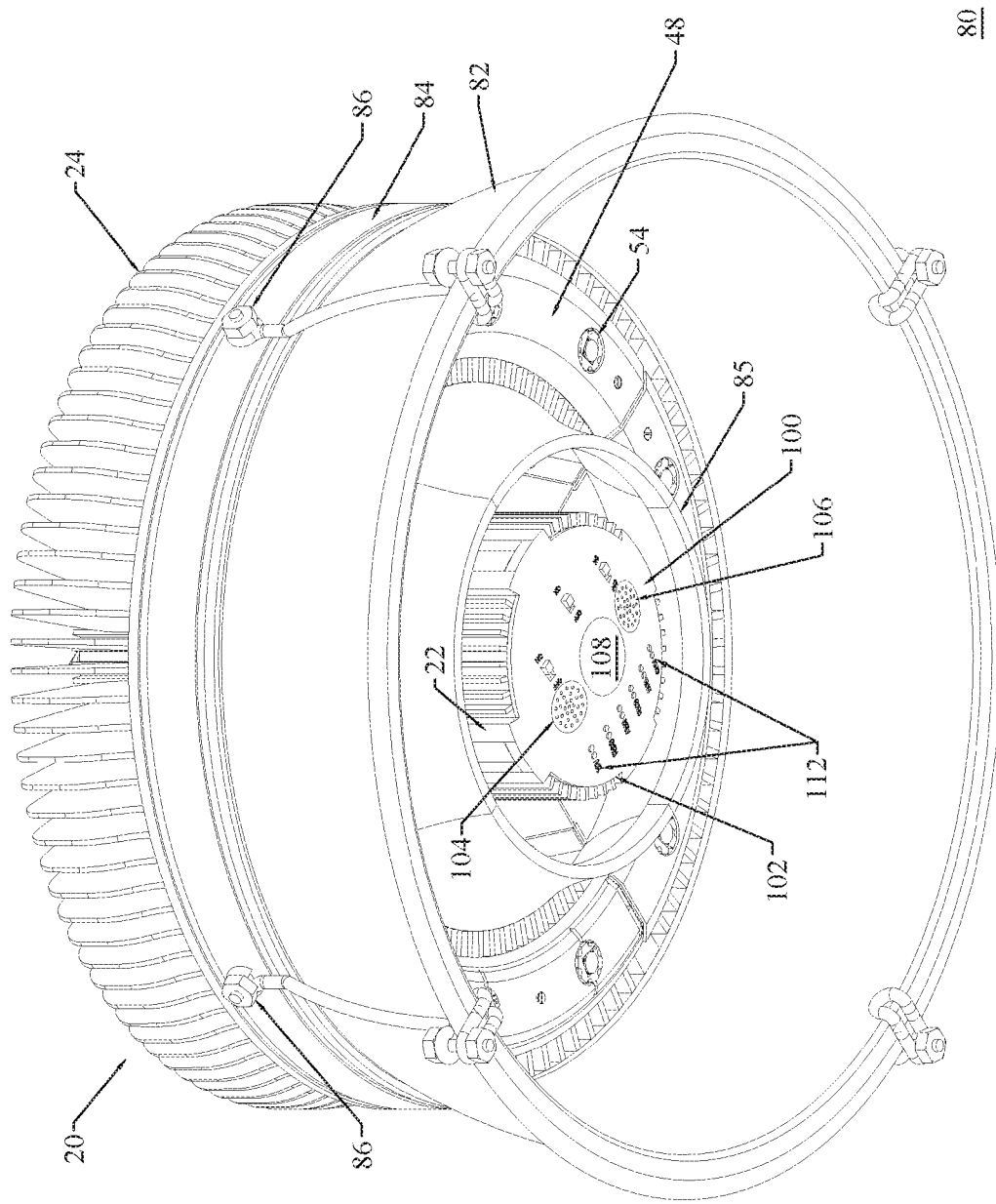
FIG. 8 shows a bottom perspective view of the LEAM of FIG. 7.

Each lamp seat 50, in the form of, for example, a direct mounted die, is configured to receive a light source 54 (see FIG. 8). Light source 54 may be any suitable lamp or light array, such as an LED lamp. Each lamp seat 50 extends inwardly into heat dissipating structure 24 so that each lamp seat 50 is generally surrounded by fins 36. The configuration of heat dissipating structure 24 with fins 36 effectively conducts heat generated by the LED light sources 54 away from LED light sources 54. Maintaining a low temperature at lamp seats 50 yields improvements in lamp energy efficiency and enhanced lifespan for the LED light sources 54.

In its centralized location in central opening 34 of heat dissipating structure 24, housing 22 functions to centralize power distribution and serves as a data receiving and transmitting hub for a LEAM that includes mechanical arrangement 20. More particularly, an electronics assembly 56, generally represented by dashed lines in FIG. 6, is retained in housing 22, and electronics assembly 56 is configured for electrically interconnecting light sources 54 (FIG. 7) to an external power source (not shown). Housing 22 can additionally contain sensory and communications devices, as will be discussed below in connection with FIG. 30. Housing 22 may include one, two, or more distinct compartments that may be defined by voltage classification. For example, alternating current (AC) line voltage devices may be placed at the top portion of housing 22, while lower AC or direct current (DC) voltage devices may reside at the bottom portion of housing 22. Power may enter housing 22 from above and may then be distributed to the various devices within electronics assembly 56.

In some embodiments, an outer surface 58 of housing 22 includes a plurality of fins 60 extending into air gap 42 (FIG. 3) between housing 22 and heat dissipating structure 24. Fins 60 effectively increase a surface are of outer surface 58 of housing 22 to facilitate rapid cooling of the housed electronics assembly 56 to yield enhanced lifespan for the components of electronics assembly 56. Accordingly, the configuration of mechanical arrangement 20 enables cool device operation by the physical separation of electronics assembly 56 in housing 22 and light sources 54 within heat dissipating structure 24, and the free flow of air around both housing 22 and heat dissipating structure 24. Furthermore, housing 22 containing electronics assembly 56 is protected from moving objects in the immediate area by the surrounding heat dissipating structure 24.

Support arms 26 provide structural support for heat dissipating structure 24 while structurally isolating structure 24 from housing 22. In some embodiments, support arms 26 may have a generally V- or U-shaped cross sectional configuration, having a top removable cover 62 (see FIGS. 1 and 3), where removable cover 62 is wider than a base 63 (see FIG. 2) of each of support arms 26. The shape of support arms 26 induces free air flow upwardly around support arms 26, again to provide effective cooling. As generally shown in FIG. 3, at least one of support arms 26 includes an interior passage 64 (revealed when cover 62 is removed) for directing wiring 66 from electronics assembly 56 (FIG. 6) retained in housing 22 to each of lamp seats 50.

Support arms 26 may additionally provide structural support for other devices (discussed in connection with FIGS. 19-28). By way of example, an exterior surface 68 of cover 62 may additionally include a plug-in receptacle 70 and mounting holes 72 formed therein. A portion of wiring 66 may be routed to plug-in receptacle 70. Thus, external devices (not shown) may be removably mounted on exterior surface 68 of at least one of support arms 26. Such an external device can include a plug element 74 (see FIG. 19) that is attachable to plug-in receptacle 70 so that the external device has communication and power connectivity to electronics assembly 56 (FIG. 6).

Accordingly, mechanical arrangement 20 provides mechanical scalability. This scalability permits flexibility in choice of light output, a particular reflector assembly, and device choice and quantity, without having to re-design the form of mechanical arrangement 20. That is, housing 22, heat dissipating structure 24, and support arms 26 of mechanical arrangement 20 enable mechanical scaling thereby allowing for the same base architecture to be used in a variety of applications. These applications may include higher light output, different optical requirements, and device mix requirements.

Figure 9:
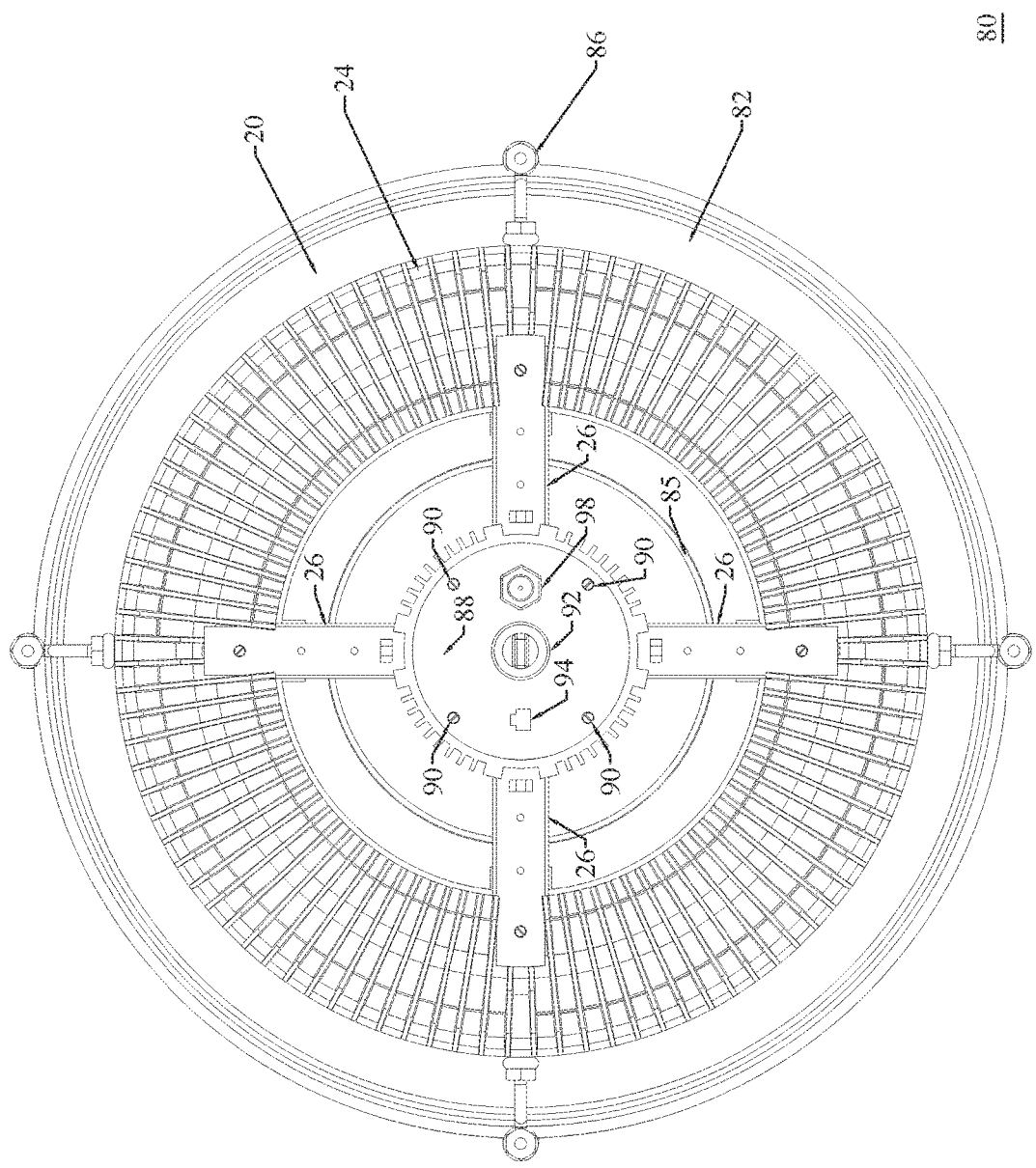
FIG. 9 shows a top view of the LEAM of FIG. 7.
Figure 10:
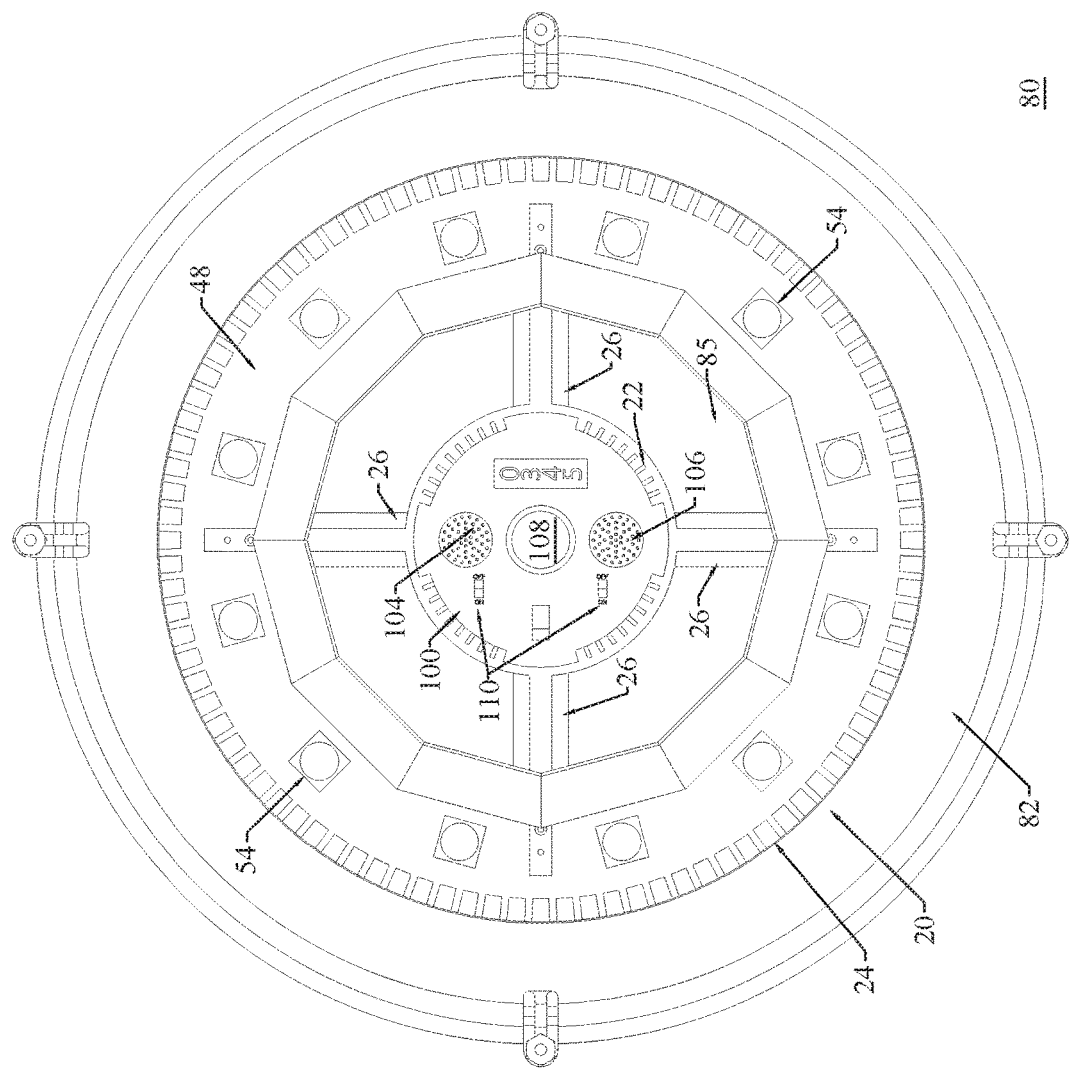
FIG. 10 shows a bottom view of the LEAM of FIG. 7.
Figure 11:
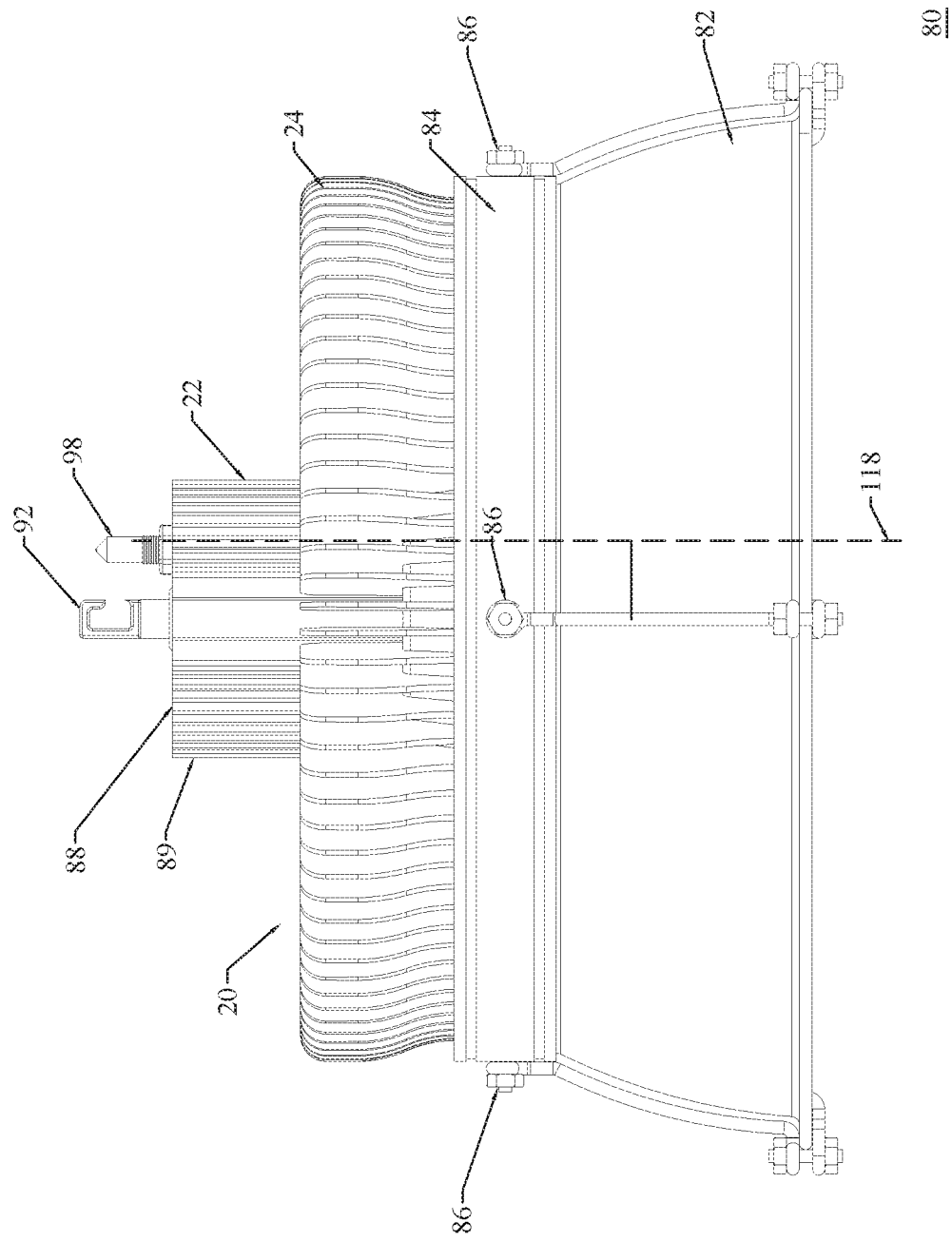
FIG. 11 shows a side view of the LEAM of FIG. 7.
Figure 12:
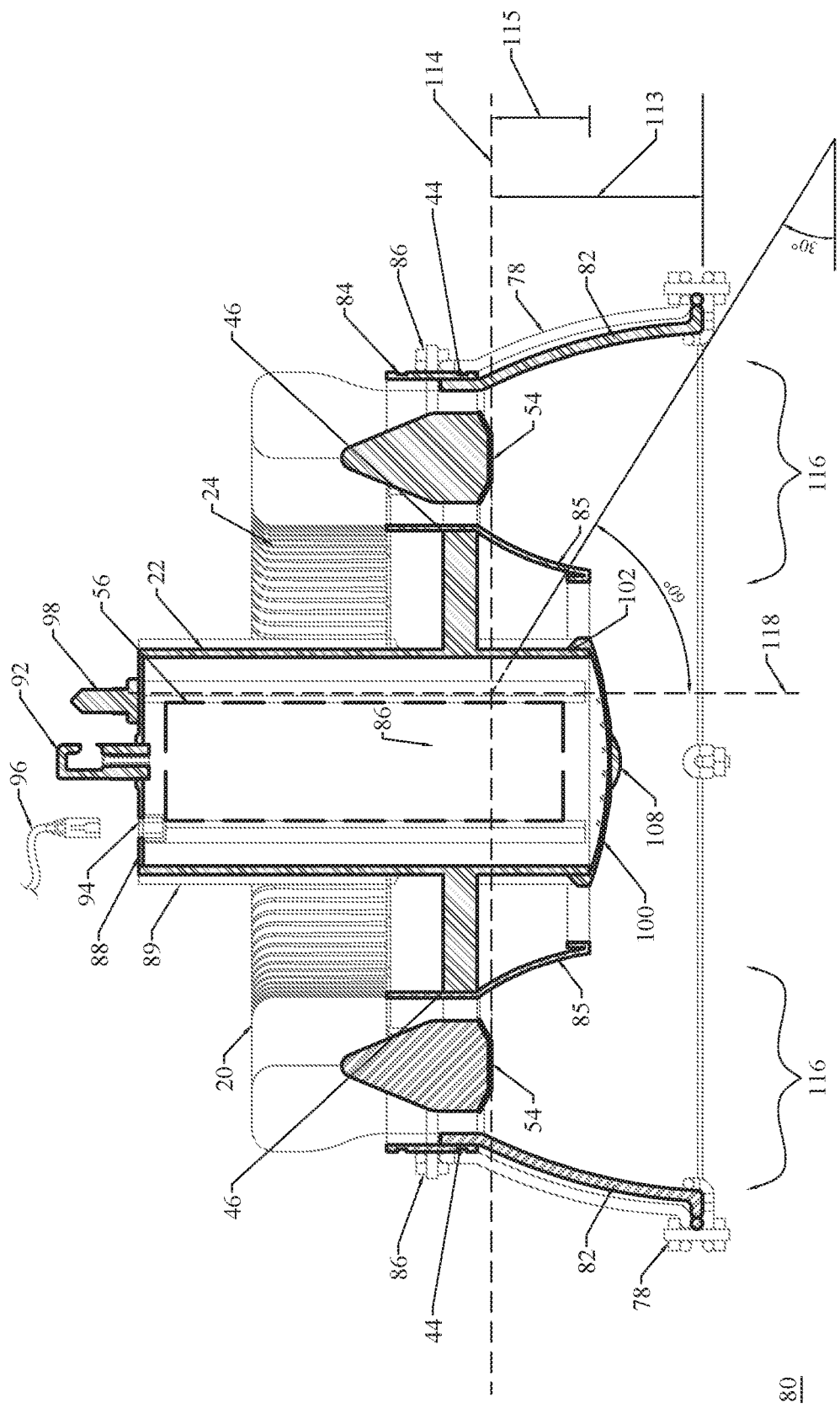
FIG. 12 shows a side sectional view of the LEAM of FIG. 7.

Referring now to FIGS. 7-12, FIG. 7 shows a top perspective view of an integrated ceiling device, referred to as a Local Environmental Area Manager (LEAM), 80 in accordance with another embodiment. FIG. 8 shows a bottom perspective view of LEAM 80. FIG. 9 shows a top view of LEAM 80. FIG. 10 shows a bottom view of LEAM 80. FIG. 11 shows a side view of LEAM 80, and FIG. 12 shows a side sectional view of LEAM 80. In general, LEAM 80 includes mechanical arrangement 20, electronics assembly 56 (generally represented in FIG. 12) retained in housing 22 of mechanical arrangement 20, and a refractor assembly 82 retained on heat dissipating structure 24 via a frame 84. In this example, frame 84 is secured to heat dissipating structure 24 via screws 86 attached to bores 47 (FIG. 1) in vertical walls 45 (FIG. 1) of heat dissipating structure 24. LEAM 80 may be adapted for use in a commercial environment where diffuse lighting, low glare, and an aesthetically pleasing appearance may be required. As such, along with refractor assembly 82, a reflector assembly 85 may be supported by support arms 26 and heat dissipating structure 24 in order to diffuse the light and/or to reduce glare from light sources 54.

As particularly shown in FIGS. 7, 9, 11, and 12, LEAM 80 includes a mounting cap 88 that couples to a top end 89 of housing 22 via fasteners 90. Mounting cap 88 may employ a conventional power hook hanger 92. Power hook hanger 92 provides a fastening means for coupling LEAM 80 to an exterior location, such as the ceiling of a building. Additionally, power hook hanger 92 is configured to enable the passage of wiring 93 (see FIG. 30) so that LEAM 80 can be powered via building power.

Mounting cap 88 may additionally include provisions for data line connectivity via a data line receptacle 94 installed in mounting cap 88 and operatively connected to electronics assembly 56. Data line receptacle 94 may be any receptacle suitable for data transfer such as, for example, an RJ45 receptacle, Universal Serial Bus (USB) receptacle, and the like. Data line receptacle 94 may be configured for attachment of a data line 96 (see FIG. 12) between electronics assembly 56 and a remote device (not shown) to enable a transfer of data to and/or from electronics assembly 56. Additionally, or alternatively, an antenna 98 may be installed in mounting cap 88. Antenna 98 may be operatively connected to electronics assembly 56. Antenna 98 may be configured for receiving and/or transmitting data between electronics assembly 56 and a remote device (not shown). Accordingly, implementation of data line receptacle 94 and/or antenna 98 enables communication between a remotely located control station or monitoring processor (not shown) and electronics assembly 56.

As particularly shown in FIGS. 8, 10, and 12, LEAM 80 further includes a removable access door 100 that couples to a bottom end 102 of housing 22. Access door 100 can enable servicing of the devices that form electronic assembly 56 retained within housing 22 of heat dissipating structure 24. Access door 100 may also incorporate one or more devices. For example, a speaker/microphone 104 and/or a smoke detector/air quality sensor 106 may be installed in access door 100. Additionally, or alternatively, a camera/occupancy sensor 108 may be installed in access door 100. Some embodiments may include multiple controllable devices that make up electronic assembly 56. Accordingly, a series of switches 110 and/or indicator lights 112 may be installed in access door 100 in order to activate/deactivate and/or monitor the operation of the devices that make up electronic assembly 56. Again, the key electronic components of light fixture 80 will be discussed in connection with FIG. 30.

Now with particular reference to FIG. 12, refractor assembly 82 is located at outer perimeter 44 of heat dissipating structure 24. Reflector assembly 85 is located at inner perimeter 46 of heat dissipating structure 24, and light sources 54 are positioned between refractor and reflector assemblies 82 and 85, respectively. Refractor assembly 82 exhibits a first height 113 extending downwardly from a location 114, i.e., the horizontal plane, of light sources 54, and reflector assembly 85 exhibits a second height 115 extending downwardly from location 114 of light source 54. In an embodiment, first height 113 is greater than second height 115. More particularly, first height 113 of refractor assembly 82 may be at least one and one quarter times greater than second height 115 of reflector assembly 85.

Together, refractor assembly 82 and reflector assembly 85 form an optical assembly 116 which is supported by, i.e., secured onto, heat dissipating structure 24. Accordingly, refractor assembly 82 may be formed from a translucent glass, or some other translucent material. Furthermore, refractor assembly 82 may employ prismatic optics. In contrast, reflector assembly 82 may be formed from a highly reflective plastic, a material having a reflective material sputtered or otherwise deposited on it, or a polished metal. Additionally, reflector assembly 85 may employ segmented optics. In an embodiment, reflector assembly 85 exhibits a profile, and in this configuration, an outwardly convex profile that is configured to redirect light emitted from light source 54 toward refractor assembly 85, as well as to downwardly direct light emitted from light source 54.

Optical assembly 116, including refractor assembly 82 and reflector assembly 85, functions to effectively redirect light from light sources 54 in order to improve light source uniformity, to increase a "glow effect," and to reduce glare. Such a structure may obtain optical efficiencies of greater than ninety-five percent. Additionally, the difference between heights 113 and 115 largely prevents direct visibility of light sources 54 over sixty degrees from nadir, where the nadir (in accordance with the Illuminating Engineering Society of North America) is defined as the angle that points directly downward, or zero degrees, from a luminaire. Accordingly, FIG. 12 shows a nadir as corresponding to a longitudinal axis 118 of LEAM 80. As further shown in FIG. 12, an approximately sixty degree angle is formed between longitudinal axis 117, i.e., the nadir, and a virtual line intersecting the bottommost edges of refractor assembly 82 and reflector assembly 85. It is known that light emitted in the eighty degree to ninety degree zone from nadir is more likely to contribute to glare. Accordingly, the difference between heights 113 and 115 effectively limits the potential for glare by directing the light within the sixty degree from nadir range.

Figure 13:
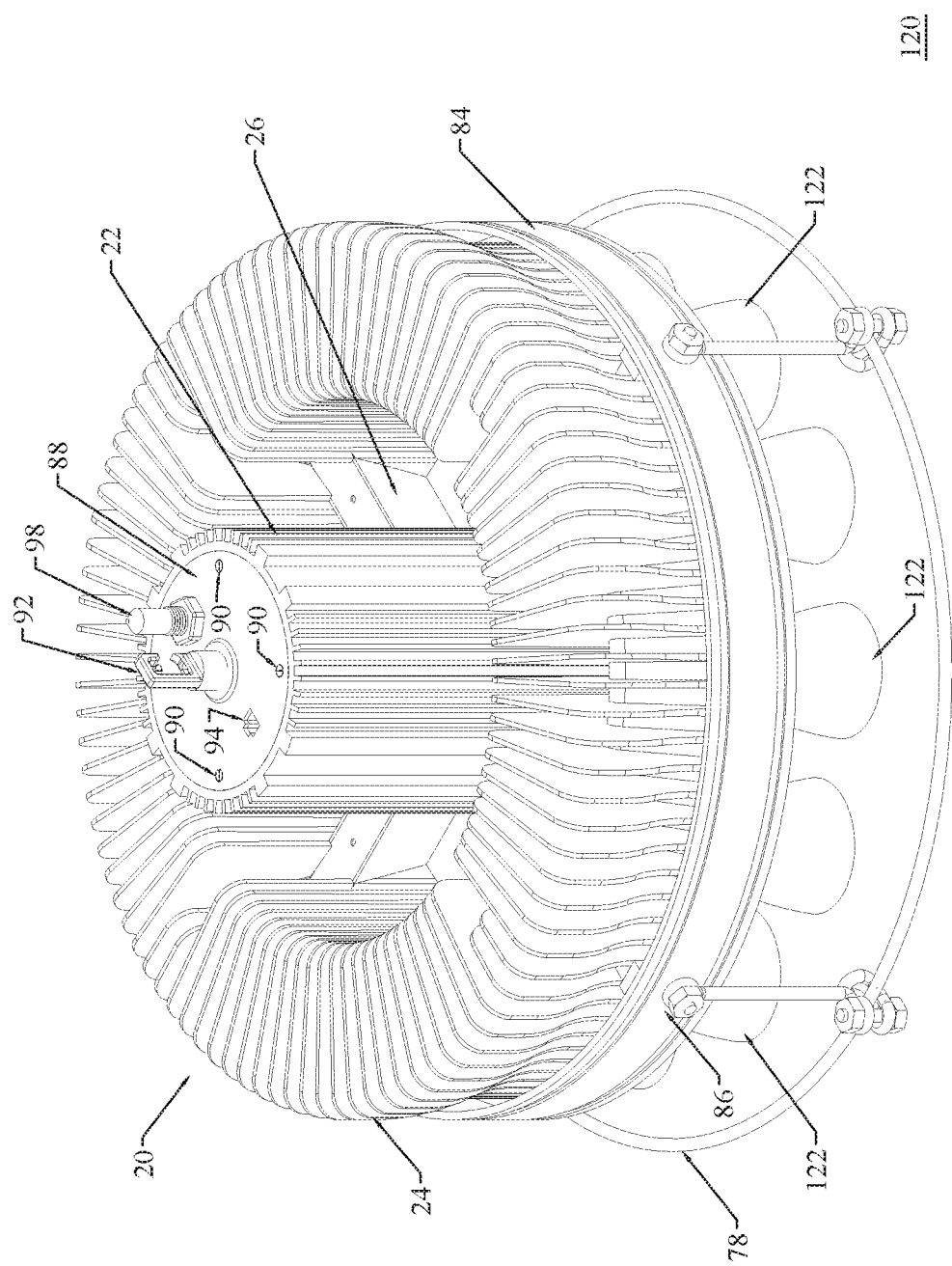
FIG. 13 shows a top perspective view of an integrated ceiling device, i.e., a LEAM, in accordance with another embodiment.
Figure 14:
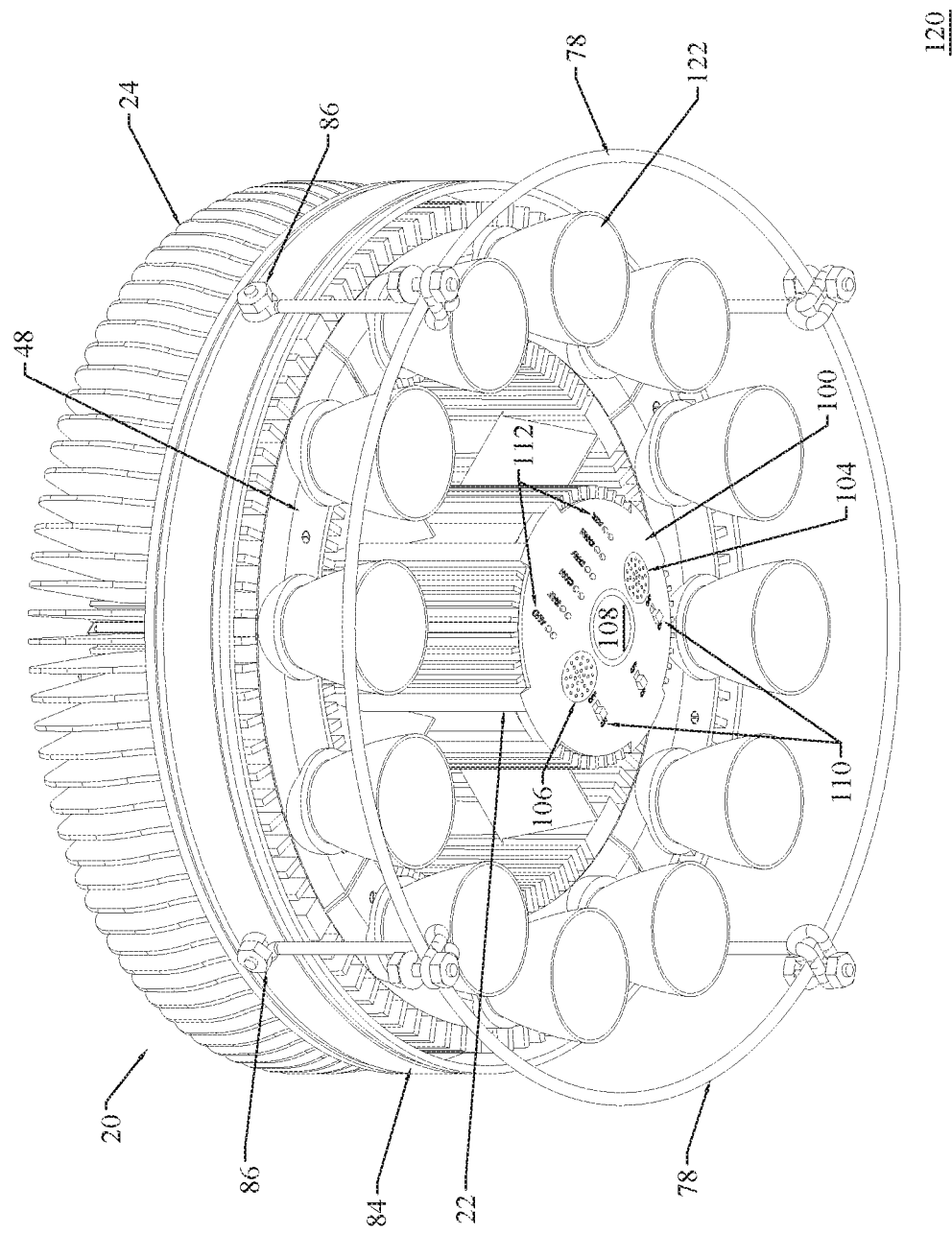
FIG. 14 shows a bottom perspective view of the LEAM of FIG. 13.
Figure 15:
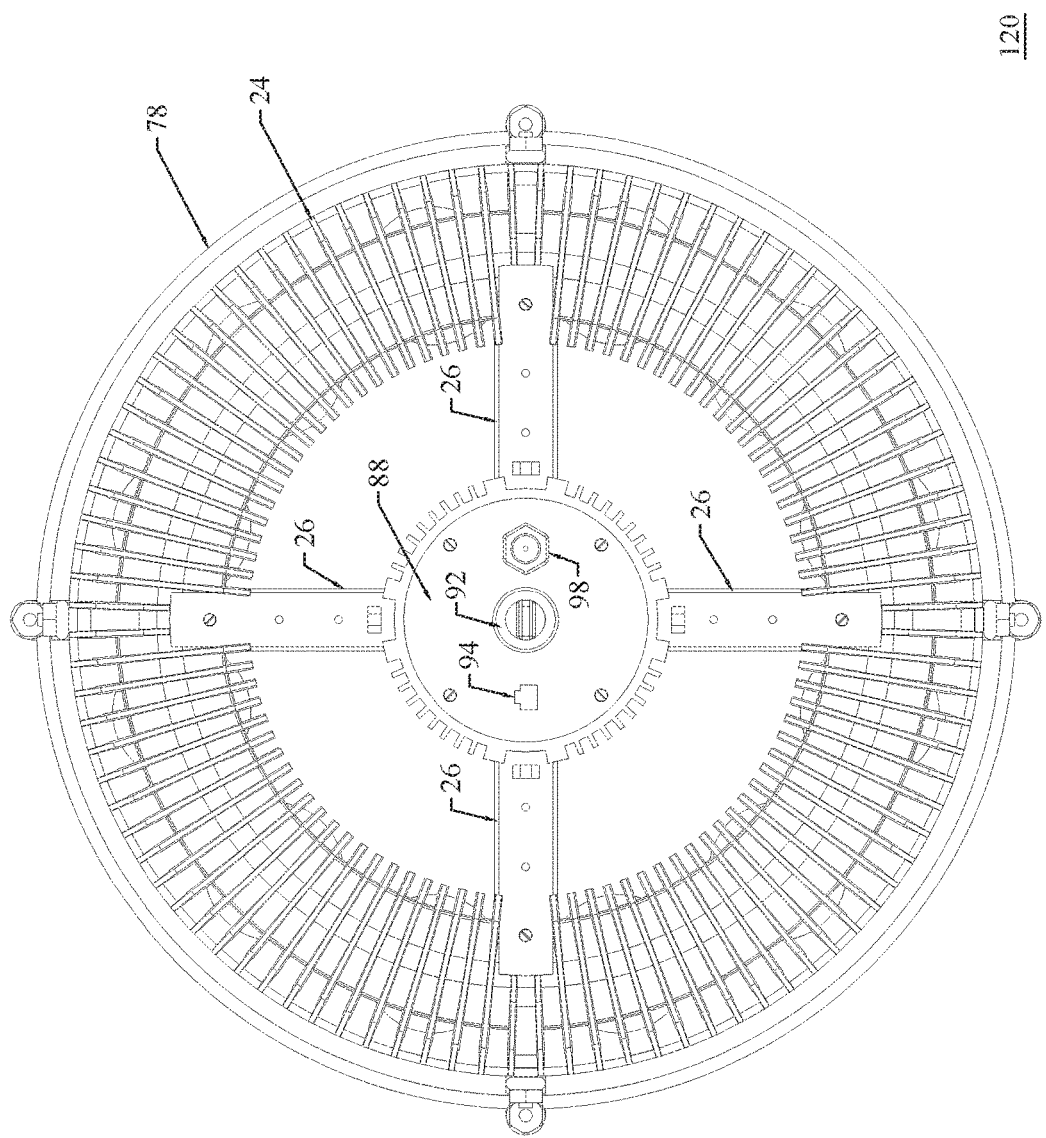
FIG. 15 shows a top view of the LEAM of FIG. 13.
Figure 16:
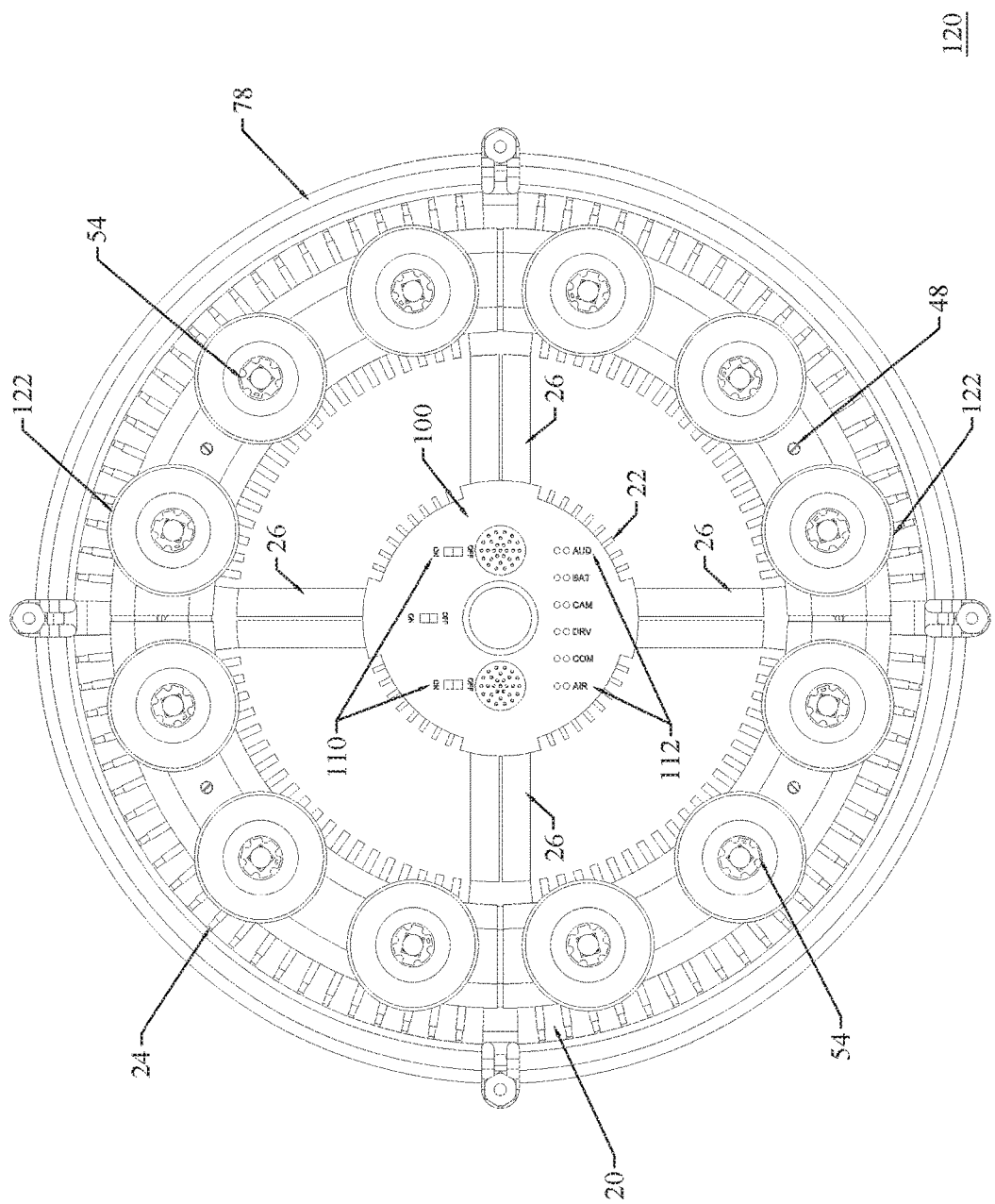
FIG. 16 shows a bottom view of the LEAM of FIG. 13.
Figure 17:
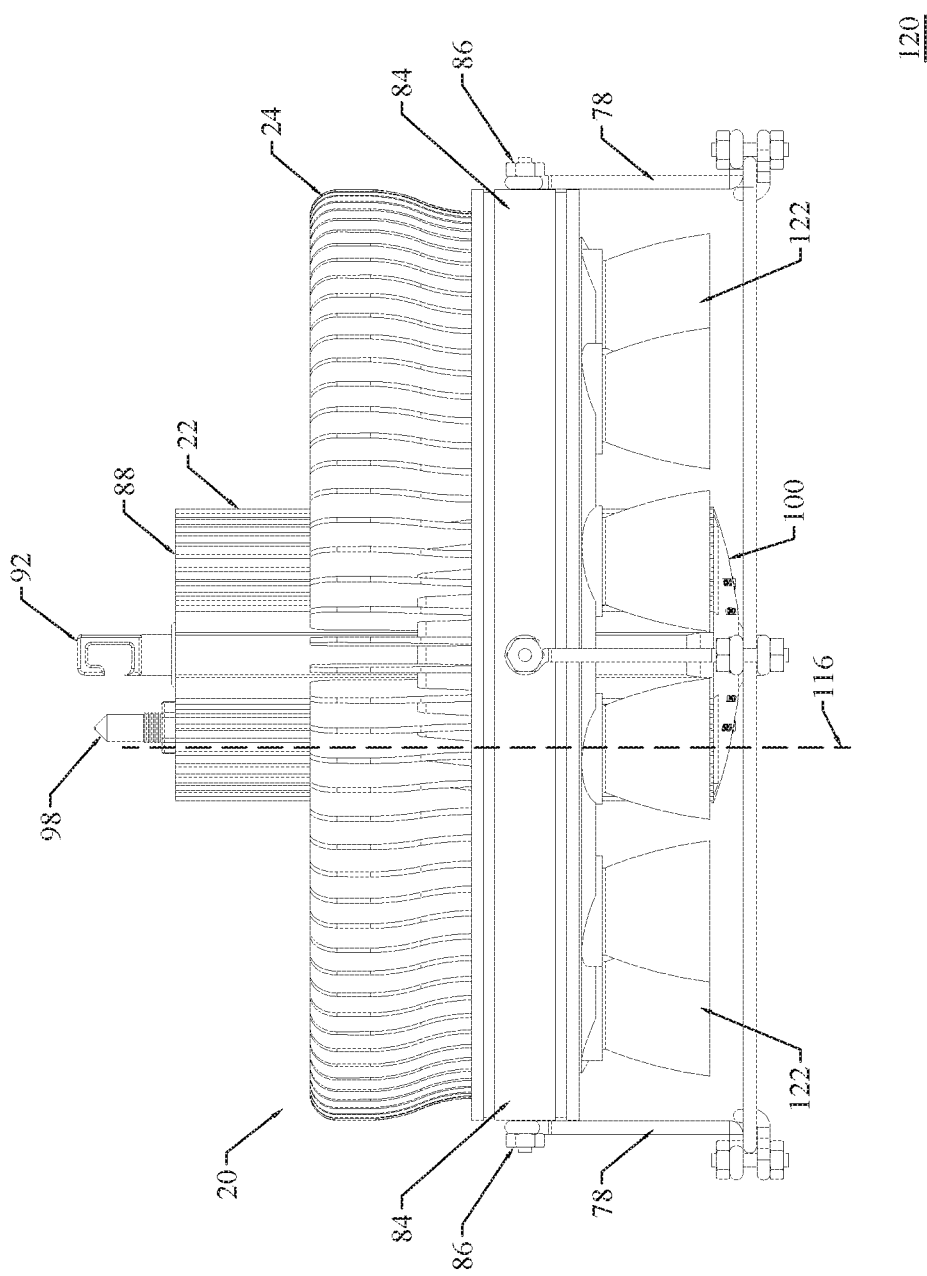
FIG. 17 shows a side view of the LEAM of FIG. 13.
Figure 18:
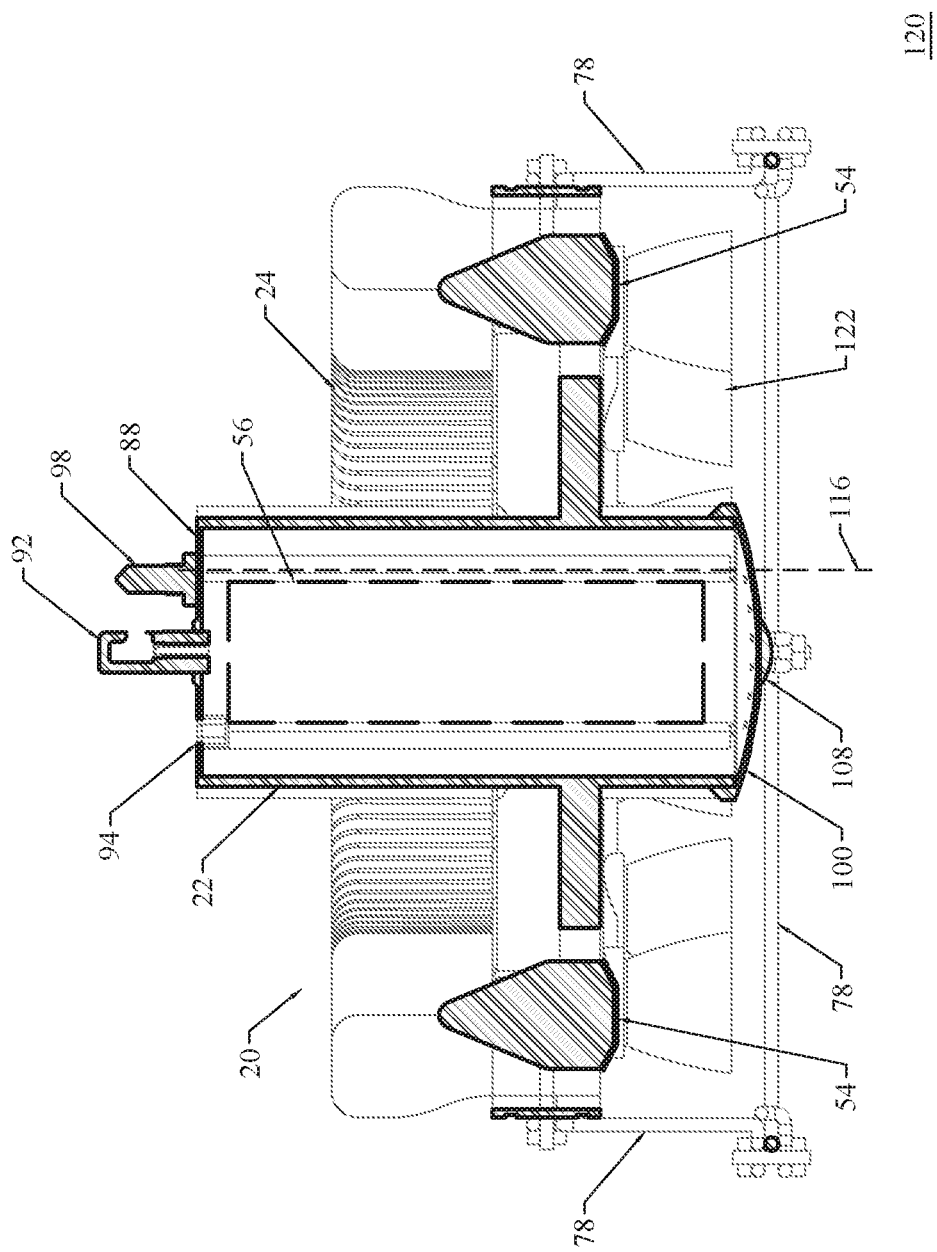
FIG. 18 shows a side sectional view of the LEAM of FIG. 13.

Referring to FIGS. 13-18, FIG. 13 shows a top perspective view of an integrated ceiling device, referred to as a Local Environmental Area Manager (LEAM), 120 in accordance with another embodiment. FIG. 14 shows a bottom perspective view of LEAM 120. FIG. 15 shows a top view of LEAM 120. FIG. 16 shows a bottom view of LEAM 120. FIG. 17 shows a side view of LEAM 120, and FIG. 18 shows a side sectional view of LEAM 120. In general, LEAM 120 includes mechanical arrangement 20, electronics assembly 56 (generally represented in FIG. 18) retained in housing 22 of mechanical arrangement 20, and frame 84 secured to heat dissipating structure 24, as described above.

Figure 7:
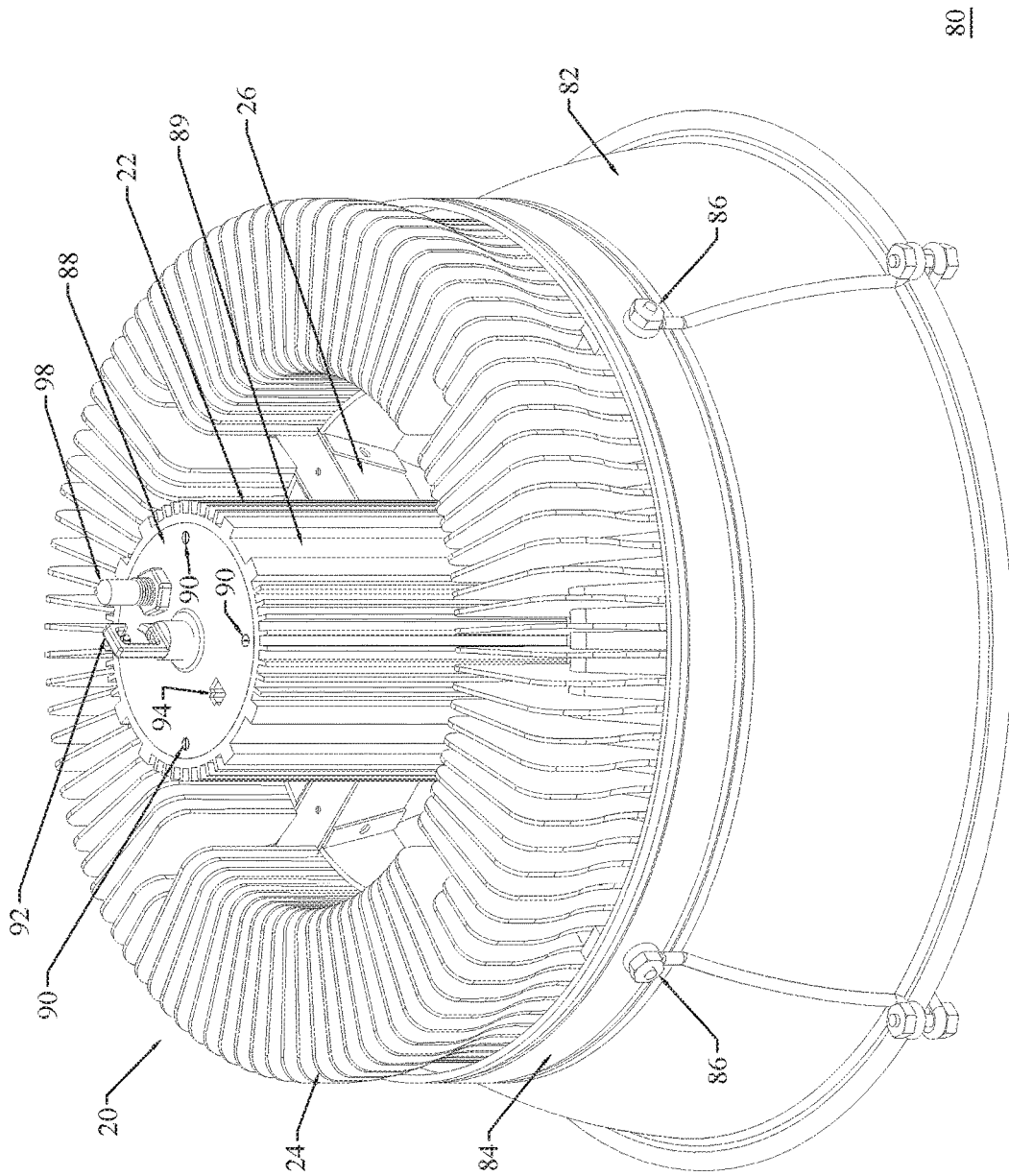
FIG. 7 shows a top perspective view of an integrated ceiling device, i.e., a LEAM, in accordance with another embodiment.

LEAM 120 may not include refractor assembly 82 and reflector assembly 85, as discussed in connection with LEAM 80 of FIG. 7. Rather, only frame 84 may be present to provide some amount of protection for light sources 54 within LEAM 120 from movable objects in the location at which LEAM 120 resides. LEAM 120 may be adapted for use in an industrial environment where high brightness and a relatively narrow beam pattern may be called for. In some configurations, LEAM 120 may include an optical assembly, supported by heat dissipating structure 24, in the form of a plurality of individual reflector assemblies 122. As such, each light source 54 is surrounded by an individual one of reflector assemblies 122. Reflector assemblies 122 may be supported or retained by bottom face 48 of heat dissipating structure 24 and support arms 26 in order to focus the light pattern from light sources 54. In some embodiments, individual reflector assemblies 122 may have different optical properties. Additionally, light sources 54 may have varying light output. Thus, a combination of reflector assemblies 122 and light sources 54 can be selected to provide a desired lighting pattern.

Like LEAM 80 (FIG. 7), LEAM 120 includes mounting cap 88 having power hook hanger 92, data line receptacle 94, and/or antenna 98 installed therein. Additionally, LEAM 120 includes access door 100 having speaker/microphone 104, smoke detector/air quality sensor 106, camera/occupancy sensor 108, switches 110 and/or indicator lights 112 incorporated therein as discussed above. Again, the key electronic components of light fixture 120 will be discussed in connection with FIG. 30.

Figure 20:
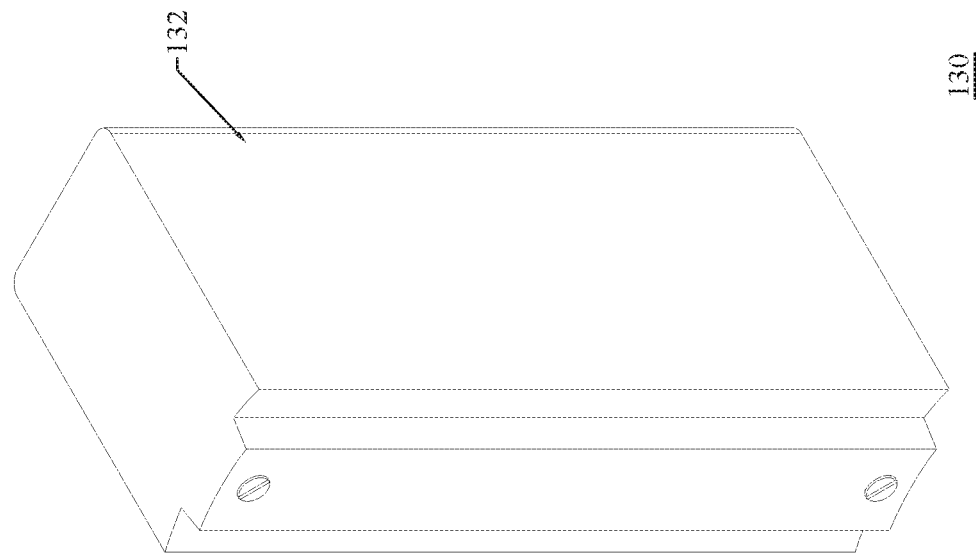
FIG. 20 shows a top perspective view of the device of FIG. 19.
Figure 19:
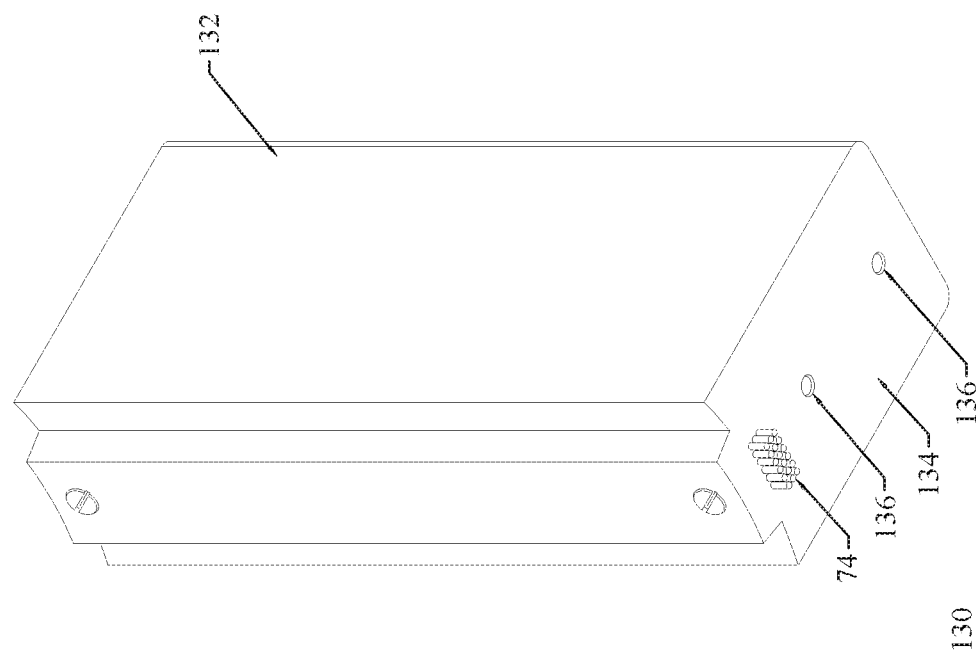
FIG. 19 shows a bottom perspective view of a device that may be mounted to the mechanical arrangement of FIG. 1 in accordance with another embodiment.
Figure 22:
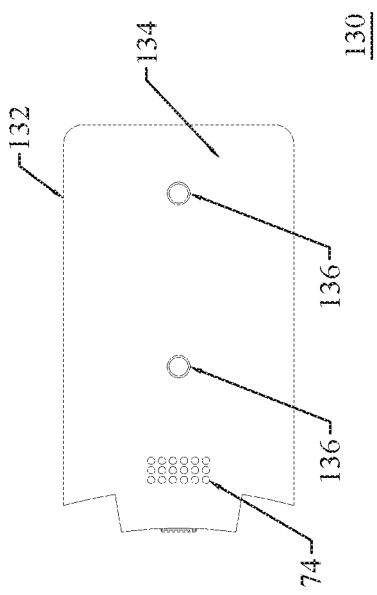
FIG. 22 shows a bottom view of the device of FIG. 19.
Figure 23:
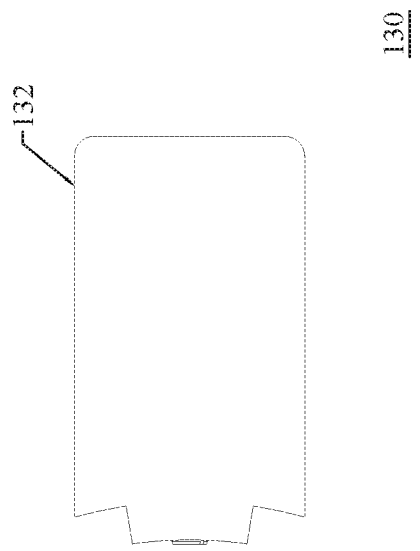
FIG. 23 shows a top view of the device of FIG. 19.
Figure 21:
FIG. 21 shows a side view of the device of FIG. 19.

Referring to FIGS. 19-23, FIG. 19 shows a bottom perspective view of a device 130 that may be mounted to mechanical arrangement 20 (FIG. 1) in accordance with another embodiment. FIG. 20 shows a top perspective view of device 130. FIG. 21 shows a side view of device 130. FIG. 22 shows a bottom view of device 130, and FIG. 23 shows a top view of device 130. In an embodiment, device 130 may be an uninterruptable power supply (UPS) that can provide emergency power when the input power source, in this case mains power, fails. Accordingly, device 130 will be referred to hereinafter as UPS 130.

UPS 130 includes a housing 132 and the necessary electronics (not shown) retained in housing 132 for supplying emergency power when incoming voltage falls below a predetermined level. The electronics may include, for example, a charger, backup battery, and DC-AC input inverter (not shown) as known to those skilled in the art. As shown in FIGS. 22 and 23, housing 132 has a profile that is adapted to interface with outer surface 58 (FIG. 1) of housing 22 (FIG. 1) of mechanical arrangement 20 (FIG. 1). A bottom surface 134 of housing 132 includes plug element 74 that is attachable to plug-in receptacle 70 (FIG. 3) formed in cover 62 (FIG. 3) of one of support arms 26 (FIG. 3) so that UPS 130 is electrically connected to electronics assembly 56 (FIG. 6), as discussed previously. Additionally, bottom surface 134 may include mounting holes 136 that mate with mounting holes 72 (FIG. 3) in cover 62. Conventional fasteners (not shown) may be utilized to fasten housing 132 to cover 62 via mounting holes 136 and mounting holes 72.

Figure 25:
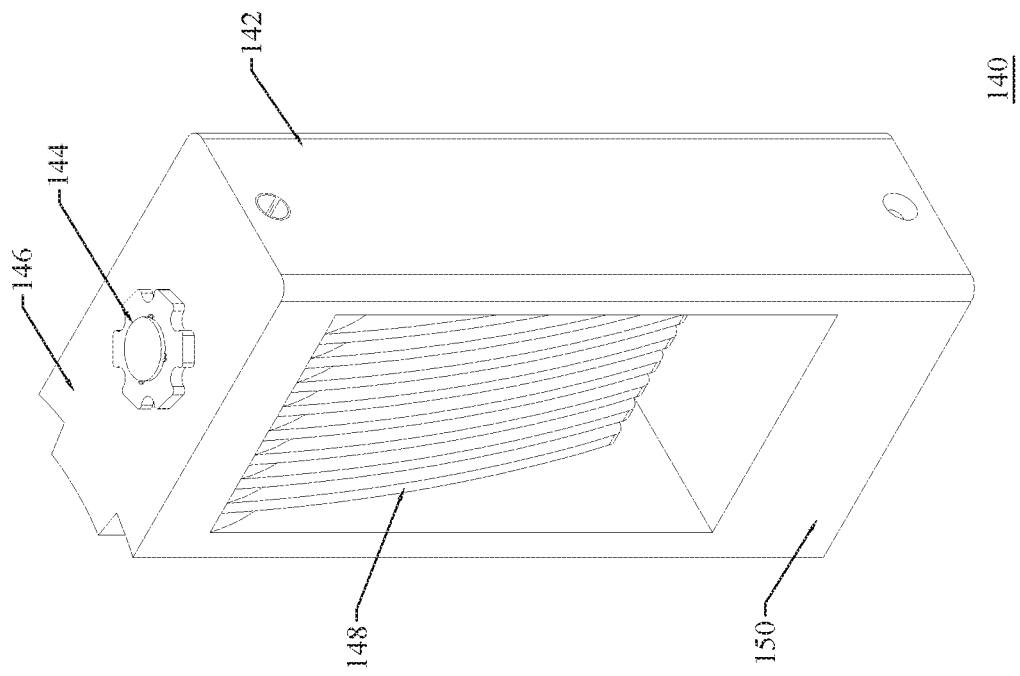
FIG. 25 shows a top perspective view of the device of FIG. 24.
Figure 24:
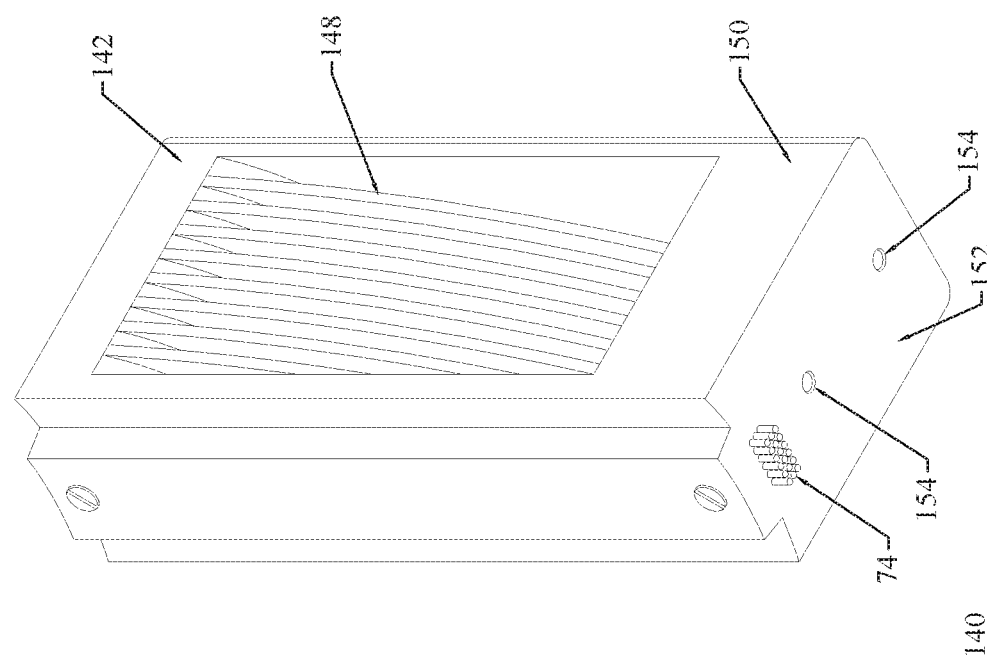
FIG. 24 shows a bottom perspective view of a device that may be mounted to the mechanical arrangement of FIG. 1 in accordance with another embodiment.
Figure 27:
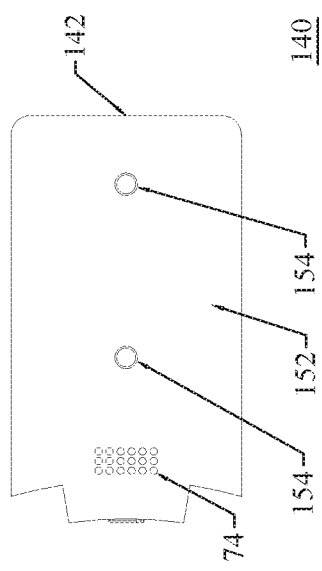
FIG. 27 shows a bottom view of the device of FIG. 24.
Figure 28:
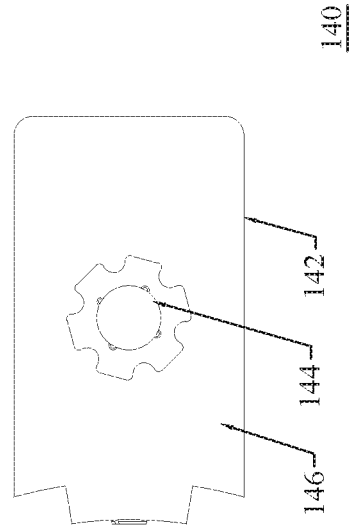
FIG. 28 shows a top view of the device of FIG. 24.
Figure 26:
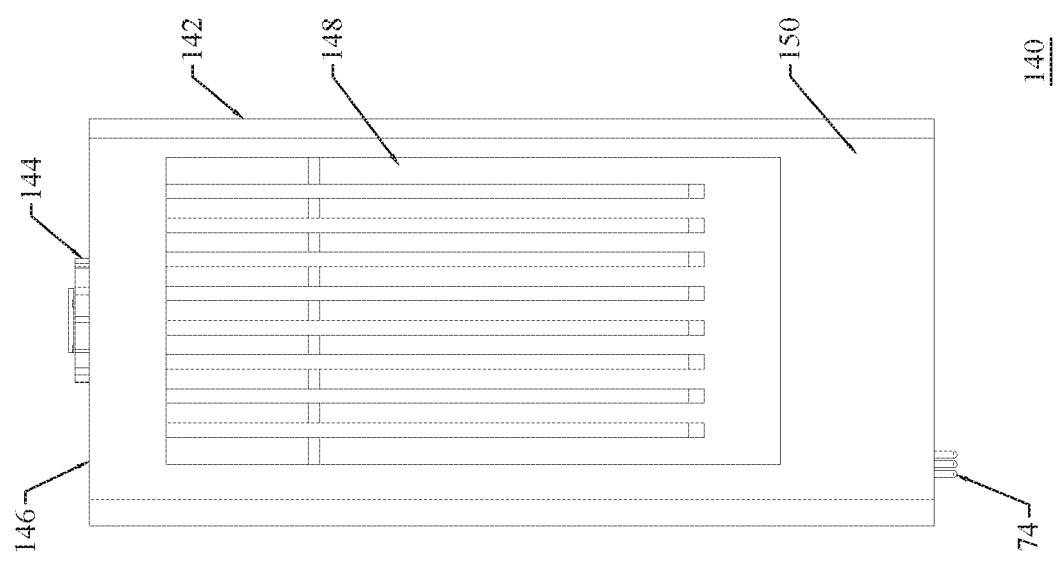
FIG. 26 shows a side view of the device of FIG. 24.

Referring to FIGS. 24-28, FIG. 24 shows a bottom perspective view of a device 140 that may be mounted to mechanical arrangement 20 (FIG. 1) in accordance with another embodiment. FIG. 25 shows a top perspective view of device 140. FIG. 26 shows a side view of device 140. FIG. 27 shows a bottom view of device 140, and FIG. 28 shows a top view of device 140. In an embodiment, device 140 may be an uplight that is positioned to cast its light in a direction opposite, for example, upwards, from the light cast by light sources 54 (FIG. 8). As such, device 140 is referred to hereinafter as uplight 140. Uplight 140 may be activated alone or along with light sources 54 during normal operation when it is desirable to cast light upwards to provide all-round indirect illumination. Alternatively, or additionally, uplight 140 may be activated during an extended loss of mains power in order to provide emergency lighting.

Uplight 140 includes a housing 142 having a light source 144 installed in a top surface 146 of housing 142. Electronics (not shown) may be retained in housing 142 for operating light source 144, as known to those skilled in the art. In some configurations, light source 144 may be an LED or any other suitable light source. Accordingly, housing 142 may include a heat sink region 148 formed in one or more side walls 150 of housing 142. Heat sink region 148 may include multiple fins that are configured to conduct the heat generated by light source 144 away from light source 144.

As shown in FIGS. 27 and 28, housing 142 has a profile that is adapted to interface with outer surface 58 (FIG. 1) of housing 22 (FIG. 1) of mechanical arrangement 20 (FIG. 1). A bottom surface 152 of housing 142 includes another plug element 74 that is attachable to plug-in receptacle 70 (FIG. 3) formed in cover 62 (FIG. 3) of one of support arms 26 (FIG. 3) so that uplight 140 can be electrically connected to electronics assembly 56 (FIG. 6), as discussed previously. Additionally, bottom surface 152 may include mounting holes 154 that mate with mounting holes 72 (FIG. 3) in cover 62. Conventional fasteners (not shown) may be utilized to fasten housing 142 to cover 62 via mounting holes 152 and mounting holes 72.

Figure 29:
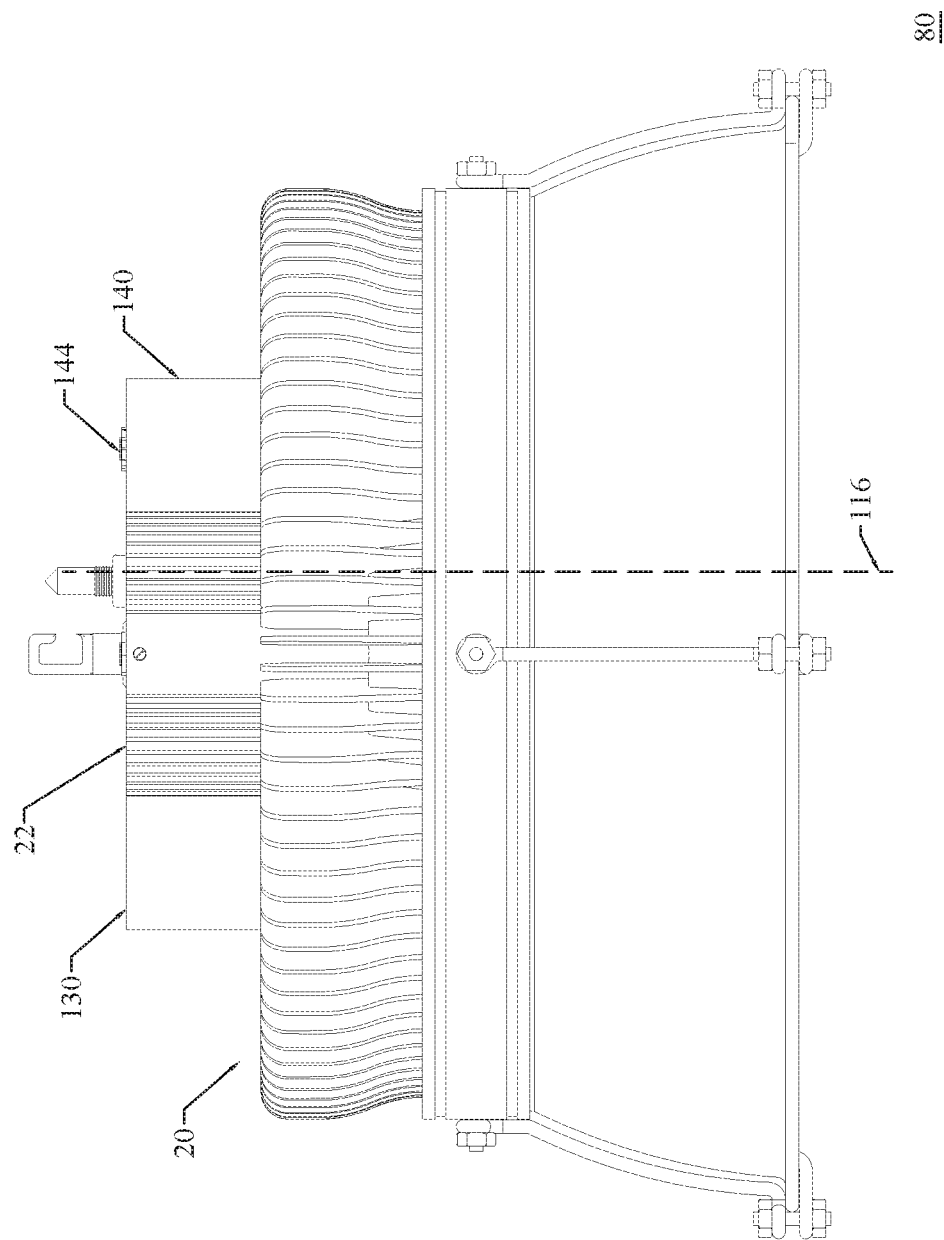
FIG. 29 shows a side view of the light fixture of FIG. 13 with the devices of FIGS. 19 and 24 retained on the light fixture.

FIG. 29 shows a side view of light fixture 80 of FIG. 13 with UPS 130 and uplight 140 retained on light fixture 80. As discussed above, each of UPS 130 and uplight 140 are removably mounted to an exterior surface of one of support arms 26 (FIG. 3). More particularly, each of UPS 130 and uplight 140 is mounted to top removable cover 62 (FIG. 3) of one of support arms 26 and abuts housing 22 of mechanical arrangement 20. Additionally, plug element 74 (FIGS. 19 and 24) of its respective UPS 130 and uplight 140 is attached with its respective plug-in receptacle 70 (FIG. 3) installed in top cover 62 so as to electrically connect UPS 130 and uplight 140 to electronics assembly 56 (FIG. 6) retained in housing 22.

Figure 30:
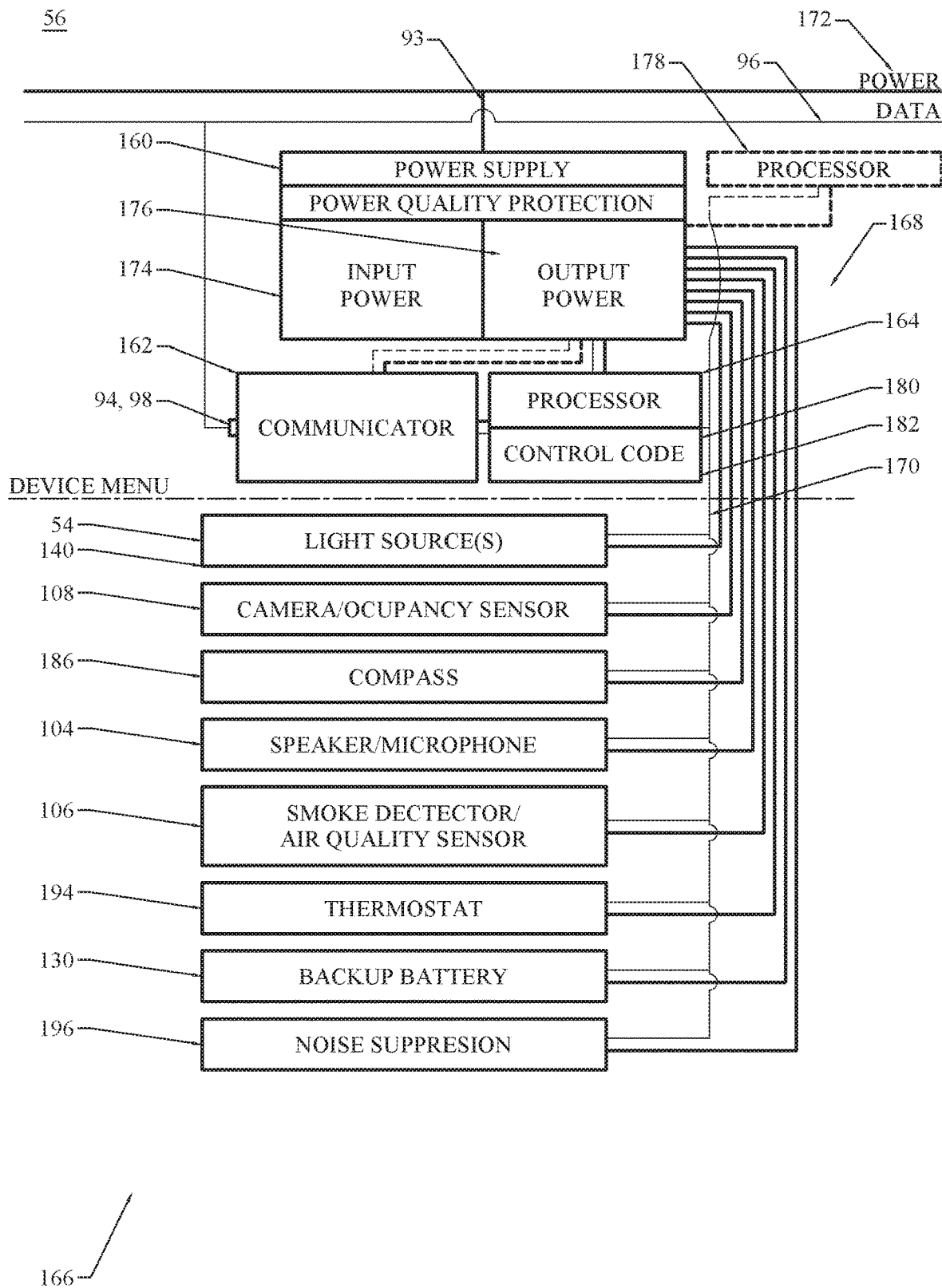
FIG. 30 shows a block diagram of an electronics assembly including a variety of devices that may be included within the electronics assembly 56 for any of the LEAMs.

FIG. 30 shows a block diagram of electronics assembly 56 including a variety of devices that may be included within electronics assembly 56 of any of LEAM 80 (FIG. 7), LEAM 120 (FIG. 13), or any of a number of LEAM designs. In general, electronics assembly 56 includes sufficient processing power coupled with sensor perception in order to emulate the human capacity of make actionable, predictable, and accurate decisions in response to environmental changes. To that end, electronics assembly 56 is capable of accepting and operating a variety of devices independently or in unison. These devices may be miniaturized to provide a broader platform for a larger number of devices with greater interactive capabilities. Thus, electronics assembly 56 may be considered a Local Environment Area Manager (LEAM) where the lighting related components provide the physical platform for the LEAM. For purposes of explanation, electronics assembly 56 will be described in connection with LEAM 80. As such reference should be made to FIGS. 7-12 concurrent with the following description.

Key components of electronics assembly 56 include one or more power supplies 160, a communicator element 162, one or more processors 164, and an array of devices 166 capable of data/signal input and output, each of which may be suitably connected via a power bus 168 (represented by solid lines) and a data bus 170 (represented by dotted lines).

In general, power supply 160 receives line power 172 via wiring 93 routed through power hook hanger 92 and converts line power 172 to the power needed to operate the various devices of electronics assembly 56. Power supply 160 may be modular and scalable having one or more input power channels 174 and output power channels 176. Input and output power channels 174, 176 may be programmable with flexibility to change the power supplied and device specific power operational parameters as needed. Power supply 160 may have an optional dedicated processor 178, represented in dashed line form, governing the power from power supply 160 while maintaining real time communication with processor 164 of electronics assembly 56. In some embodiments, power supply 160 may also have direct communication capability with an external network (not shown).

Data output from power supply 160 may include reporting on the quality of the input power, the operational temperature of power supply 160, the power consumption of power supply 160 including client devices such as communicator element 162, processor 164, and array of devices 166, time of usage broken down by device, and operational anomalies. Power supply 160 processes the highest electrical load of electronics assembly 56. Therefore, power supply 160 may be located in the upper region or an upper compartment of housing 22. The upper region of housing 22 has three hundred and sixty horizontal degrees of exposure to cooling air circulation and full exposure to cooling air at mounting cap 88 for providing effective cooling to the housed power supply 160. The circuit boards (not shown) for power supply 160 may be wired by a conventional method or engaged by plug-in connectors. Additionally, the circuit boards may be encased or open and may be secured directly to housing 22 by mounting them along the inner perimeter of housing 22.

As a local environment area manager, electronics assembly 56 includes communicator element 162 in order to permit direct or via processor 164 communication with onboard array of devices 166. Additionally, communicator element 162 may be configured to enable communication between a plurality of LEAMs 80, to enable communication with a local or remote building management system, and/or with local or remote clients. Such clients could be corporate offices or first responders needing real time input about a specific location in a building. Communicator element 162 may employ radio frequency (RF) communication via antenna 98, power line communication (PLC) carrying data on the mains power line carrying line power 172, a dedicated data line such as data line 96 connected with data line receptacle 94, or any combination thereof.

In some embodiments, each LEAM 80 may be initialized with a unique address and an optional ability to assign a sub-address to all devices within LEAM 80. In this manner, the operational integrity of the various elements of electronics assembly 56 may be monitored and any anomalies with onboard devices may be alerted, identifying the nature of the anomaly and possible recommendations for action.

Processor 164 can contain resident memory 180 that may be programmed with control code 182 prior to delivery to a building, during commissioning, or at any time thereafter. Programming may be performed by a wired connection to a port, e.g., data line 96 connected to data line receptacle 94 or wirelessly via antenna 98. System updates and device specific updates to control code 182 may occasionally be performed with occasional device upgrades.

Processor 164, executing control code 182, may be configured to receive local device sensory input from one or more devices of array 166, and then compile this information in accordance with pre-programmed instructions. Processed information may then be converted to actionable output to array of devices 166. In addition, processor 164 may communicate with neighboring or remote devices and may transmit instructions, instructions and data, or instructions, data and images. Processing power may vary among electronic assemblies 56 of a variety of LEAMs, based on the application's specific needs.

Control code 182 may be multi-device relational software designed to operate array of devices 166 in unison. Control code 182 may be scalable by modules, where each module relates to the functionality of an associated device and its relation to other onboard devices and the entire network's devices. Control code 182 may be provided with input tables such as schedules and set points, as well as alert parameters and operational reports. In addition, control code 182 can be customized for specific applications and may include self-learning modules. Processor 164 has sufficient memory 180 associated therewith in order to access and act on pertinent information in real time. Additionally, control code 182 may be provided with a self-reporting module associated with each device in array 166 in order to report the device's operational condition and provide alerts when the device performs outside its optimal performance range.

Array of devices 166 includes light sources 54 and uplight 140, and may include one or all of the following: camera 108; a compass 186; speaker/microphone 104 or a combination thereof; smoke detector/air quality sensor 106; an occupancy sensor 192; a thermostat 194; a backup battery, e.g., UPS 130 (FIG. 19); and noise suppression circuitry 196. The devices presented in array 166 should not be considered to be all inclusive. That is, the devices represented in array 166 may additionally include other building system and monitoring devices and circuits not listed herein.

The various devices within array 166 may be utilized in connection with comfort control, life safety, loss prevention, marketing analysis, asset management functions, and/or operational optimization. Comfort control may entail lighting uniformity, sound control including suppression, temperature control, air quality control, and so forth. Life safety may entail air quality monitoring, local and remote alarming, lighting and sound delineation of egress pathway, live feed to first responders, the identification of "hot spots" in event of fire or crime, and so forth. Loss prevention may entail system alarming for operational anomalies, theft prevention via behavioral software analysis, produce spoilage avoidance by monitoring local ambient air temperature, and so forth. Marketing analysis may entail monitoring or customer traffic pattern, customer behavior, customer gender, cash register wait time, customer volume, customer time of day week and month visit, customer demographics, and so forth. Asset management may entail space utilization reporting, facility design performance analysis, asset inventory control, asset depreciation record, and so forth. Operational optimization may entail energy usage monitoring, reduction in maintenance men hours via event and alarms reporting, event recordation, product and system performance evaluation, and so forth.

A key feature of LEAMs 80, 120 having mechanical arrangement 20 is the optimization of exposure to the surrounding cooling air and airflow at least two hundred and seventy degrees across the vertical axis of heat dissipating structure 24, as well as the vertical and horizontal axes of housing 22. The form of mechanical arrangement 20 is determined by its three key components, i.e., heat dissipating structure 24 at the perimeter of mechanical arrangement 20, housing 22 at the center of mechanical arrangement 20, and support arms 26 bridging between structure 24 and housing 22 through which power flows to light sources 54 in heat dissipating structure 24. The form of mechanical arrangement 20 is critical to superior thermal heat management of LEAMs 80, 120.

Another key feature of LEAMs 80, 120 having mechanical arrangement 20 and electronics assembly 56 is the capability to mount lighting and non-lighting related environment sensory devices (e.g., speaker/microphone 104, smoke detector/air quality sensor 106, and camera/occupancy sensor 108) in access door 100 at bottom end 102 of housing 22, as well as mounting communication devices (e.g., data line receptacle 94 and antenna 98) in mounting cap 88 at top end 89 of housing 22. With the proximity of communication devices to the power entry for LEAMs 80, 120 at power hook hanger 92, efficiencies are achieved due to centralized placement location for the lighting and non-lighting related devices. Moreover, the separation between the housed electronics assembly 56 and light sources 54 enables effective cooling of the housed electronics assembly 56, as well as protection from exterior forces.

Another key feature of LEAMs 80, 120 with centrally located housing 22 is the capability to access power supply 160 at bottom end 102 of housing 22 via removably mounted access door 100. Certain components, such as power supply 160 may be readily and quickly inserted and removed through guiding slots on an inner perimeter of housing 22. Since access door 100 is removable, all devices within housing 22 may be equipped with a quick disconnect in order to install, remove, and replace any of the devices within housing 22.

Yet another key feature of LEAMs 80, 120 includes the capability to provide backup emergency battery, e.g., UPS 130, whose power may be selectively distributed to all essential services and devices during an emergency, which can be received either from a light fixture driver or a secondary step-down power device. In some embodiments, UPS 130 may be connected to the light fixture audio system, e.g., speaker/microphone 104. Additionally, UPS 130 may be networked with other input/output onboard environmental data collection, assessment, and operational devices, and have remote communication capability.

Another key feature of LEAMs 80, 120 includes an emergency light system, e.g., light sources 54, that may be used to delineate an egress path by supplementing the ambient light level to identify the directionality of the path to egress doors. This down light feature, using light sources 54 may be supplemental with a strobe light. In some embodiments, speaker/microphone 104 may be used to broadcast a pathway direction identifier.

Another key feature of LEAMs 80, 120 is the capability to operate one or several onboard devices from array 166, such as backup battery 130, speaker/microphone 104, smoke detector/air quality sensor 106, camera/occupancy sensor 108, communicator element 162, and compass 186 in unison, based on real time information processed and programmed instructions.

A key feature of LEAMs 80, 120 having electronics assembly 56 entails the capability to perform auto-commissioning of a network of light fixtures 80. For example, each of LEAMs 80, 120 includes a discrete address, camera 108, communicator element 162, processor 164 and/or remote processors. Processor 164 and/or the remote processors may include an electronic map showing each of LEAMs 80, 120 by its associated discrete address and its relative location to the entire network of LEAMs 80, 120. Auto-commissioning commences following association of one LEAMs 80, 120 with its corresponding placement on the electronic map.

Another key feature of LEAMs 80, 120 having electronics assembly 56 entails light control at its local location. For example, each of LEAMs 80, 120 includes a discrete address, camera 108 with an integrated light meter, compass 186, communicator element 162, processor 164 and/or remote processors. Processor 164 and/or the remote processors may maintain a pre-determined light level by dimming or turning LEAMs 80, 120 on or off through processing in real time local zone illumination conditions data obtained by camera 108 and preprogrammed local or remote controller instructions.

Another key feature of LEAMs 80, 120 having electronics assembly 56 entails the optimization of local and entire space environmental conditions. Optimization methodology may utilize data from camera 108, occupancy sensor 192, as well as other onboard sensor devices such as processor 164, thermostat 194, communicator element 162, processor 164 and/or remote processors to process data and act in real time on changing conditions while operating within programmatic instruction guidelines.

Another key feature of LEAMs 80, 120 having electronics assembly 56 entails the capability to collect environmental conditions data via camera 108 and relay the data to local processor 164 and/or remote processors. The data collected by camera 108 may include, but is not limited to, the functionally of devices such as in occupancy sensing, a light meter output, a traffic count, human load density analysis, time of day activity logging, and photographic and thermal imagery. The processed data obtained by camera 108 with or without additional information processed from other non-camera devices within LEAMs 80, 120 facilitate optimal operation of LEAMs 80, 120.

Another key feature of LEAMs 80, 120 having electronics assembly 56 entails the capability to function as a public announcement, sound, and alarming system through the provision of audio input/output via microphone/speaker 104. Additionally, microphone/speaker 104 may be networked with other input/output onboard environment data collection, assessment, and operational devices, and have remote communication capability.

Another key feature of LEAMs 80, 120 having electronics assembly 56 entails the implementation of smoke detector/ air quality sensor 106. Smoke detector/air quality sensor 106 may also be networked with other input/output onboard environmental data collection, assessment, and operational devices, and have remote communication capability.

In summary, embodiments described above resolve a number of the mechanical, thermal, electrical, and architectural challenges that are commonly associated with integrated ceiling system devices and particularly with high-output LED light fixture design. Furthermore, the structural configuration of the LEAM makes the LEAM suitable for use in a wide variety of environments, such as, commercial, institutional, and industrial applications. Additionally, the LEAM including the mechanical arrangement and electronics assembly may assume partial or full control over the ambient environment in the vicinity of the LEAM, integrating operational logic traditionally associated with isolated disciplines' networks of heating, ventilation, and air conditioning (HVAC) monitoring devices, fire protection devices, air quality monitoring devices, input/output audio devices, temperature and humidity devices, security and normal operation monitoring cameras, occupancy sensors, lighting controls, and so forth. Consequently, the LEAM including the mechanical arrangement and the electronics assembly yields significant improvements in terms of the integration of a variety of building system functions combined with the quintessential need for suitable ambient lighting in an aesthetically pleasing form factor.

While the principles of the inventive subject matter have been described above in connection with specific apparatus configurations described above, it is to be clearly understood that this description is made only by way of example and not as a limitation on the scope of the inventive subject matter. For example, embodiments may be implemented in systems having other architectures as well. The various functions or processing blocks discussed herein and illustrated in the Figures may be implemented in hardware, firmware, software or any combination thereof. Further, the phraseology or terminology employed herein is for the purpose of description and not of limitation.

The foregoing description of specific embodiments reveals the general nature of the inventive subject matter sufficiently so that others can, by applying current knowledge, readily modify and/or adapt it for various applications without departing from the general concept. Therefore, such adaptations and modifications are within the meaning and range of equivalents of the disclosed embodiments. The inventive subject matter embraces all such alternatives, modifications, equivalents, and variations as fall within the spirit and broad scope of the appended claims.

The invention claimed is:

1. An integrated ceiling device comprising:
a mechanical arrangement comprising
an enclosed housing retaining an electrical assembly,
a heat dissipating structure comprising a heat sink coupled to a plurality of monolithically formed heat dissipating fins, and
at least one light source thermally and mechanically coupled to the heat dissipating structure,
wherein at least one of the plurality of monolithically formed heat dissipating fins is disposed on a peripheral wall of the heat sink and protrudes outward therefrom,
wherein the enclosed housing is isolated, separated, and offset from the heat dissipating structure to define a through air gap between the enclosed housing and the heat dissipating structure to permit free flow of air through the through air gap,
wherein the enclosed housing extends above the heat dissipating structure and is positioned about a central vertical axis of the heat dissipating structure, and
wherein the enclosed housing is mechanically and electrically coupled to the heat dissipating structure and cool air flowing freely from below, between, and around the at least one of the plurality of monolithically formed heat dissipating fins removes hot air formed above the heat dissipating structure, in the through air gap between the enclosed housing and the heat dissipating structure coupled to the at least one light source, and around surfaces of the enclosed housing.

2. The device of claim 1, wherein the at least one light source coupled to the heat sink directs light in a direction opposite to a surface the light source is coupled to.

3. The device of claim 1, wherein the monolithically formed heat dissipating fins are disposed at least on an outer perimeter of the heat sink.

4. The device of claim 1, wherein an outer surface of the housing comprises a plurality of heat dissipating fins.

5. The device of claim 1, further comprising: an optical assembly coupled to the heat dissipating structure.

6. The device of claim 5, wherein the optical assembly is coupled to the at least one light source retained by the heat dissipating structure, and wherein the optical assembly comprises a least one of a refractor and a reflector.

7. The device of claim 1, wherein the at least one light source is a first light source, wherein the mechanical arrangement further comprises a second light source disposed above the first light source, and wherein the first light source directs light in a first direction substantially perpendicular to a surface of the heat sink that the first light source is coupled to and the second light source directs light in a second direction opposite to the first direction.

8. The device of claim 1, further comprising: a removable access cover coupled to the housing.

9. The device of claim 8, wherein at least one electronic device is coupled to the removable access cover of the housing.

10. The device of claim 1, wherein the heat sink has a customizable form.

11. The device of claim 1, further comprising: an electronic component externally mounted to at least one of the housing and an arm.

12. The device of claim 1, wherein the electrical assembly includes at least one of: a communication device, a sensing device, a processing device, an output device, and a power supply device.

13. An integrated ceiling device comprising:
a mechanical arrangement comprising an enclosed housing retaining an electrical assembly, a heat dissipating structure comprising a heat sink coupled to a plurality of monolithically formed heat dissipating fins, and a plurality of light sources thermally and mechanically coupled to the heat sink,
wherein at least one of the plurality of monolithically formed heat dissipating fins extends outward upward from a peripheral wall of the heat sink to form a protective contact surface that protects the housing,
wherein the enclosed housing is isolated, separated, and offset from the heat dissipating structure to define a through air gap between the enclosed housing and the heat dissipating structure open to free flow of air through the through air gap, wherein the enclosed housing extends above the heat dissipating structure and is disposed about an interior vertical axis of the heat dissipating structure, and wherein at least a portion of the enclosed housing is mechanically and electrically coupled to the heat dissipating structure and at least a bottom surface of the enclosed housing is cooled by air flowing freely from below, between, and around the at least one of the plurality of monolithically formed heat dissipating fins extending outward from the peripheral wall of the heat sink to remove hot air formed above the heat dissipating structure, in the through air gap, and around a surface of the housing.

14. The device of claim 13, wherein at least one of the plurality of light sources coupled to the heat sink directs light in a direction substantially perpendicular to a surface the light source is coupled to.

15. The device of claim 14, wherein the heat sink has a customizable form.

16. The device of claim 13, wherein the monolithically formed heat dissipating fins coupled to the heat sink are disposed at least on a perimeter of the heat sink.

17. The device of claim 13, further comprising an optical assembly coupled to at least one light source of the plurality of light sources.

18. The device of claim 17, wherein the optical assembly coupled to the at least one light source is retained by the heat dissipating structure and comprises at least one of a refractor and a reflector.

19. The device of claim 13, wherein at least one of the plurality of light sources is configured to direct light in a direction away from the heat dissipating structure of the mechanical arrangement, and wherein at least one of the plurality of light sources is coupled to the heat dissipating structure.

20. The device of claim 19, wherein a first light source and a second light source of the plurality of light sources are configured to direct light in a direction opposite that of one another.

21. The device of claim 20, wherein one of the light sources is operable independently from a second light source and directs light in an opposite direction.

22. The device of claim 20, wherein at least one light source is an indirect light source emitting the light all-around the device.

23. The device of claim 13, wherein at least one of the plurality of light sources is configured to be remotely controlled.

24. An integrated ceiling device comprising:
a mechanical arrangement including:
an enclosed housing retaining electronic devices;
a heat dissipating structure including a heat sink having a plurality of monolithically formed heat dissipating fins, wherein at least one of the plurality of monolithically formed heat dissipating fins extends outward from a perimeter of the heat sink to protect the electronic devices from moving objects; and
a light source thermally and mechanically coupled to the heat dissipating structure,
wherein the enclosed housing is isolated, separate, and offset from the heat dissipating structure coupled to the plurality of monolithically formed heat dissipating fins to define an air gap therebetween,
wherein the enclosed housing extends above the heat dissipating structure and is disposed about a central vertical axis of the heat dissipating structure,
wherein the enclosed housing is mechanically and electrically coupled to the heat dissipating structure, and
wherein the electronic devices generate heat during operation and free flowing air from below, flowing between and around the plurality of heat dissipating fins cools at least an exterior surface between the enclosed housing and the heat dissipating structure.

* * * * *